(12) United States Patent
    Rajaraman et al.

(10) Patent No.: US 12,577,517 B2
(45) Date of Patent: *Mar. 17, 2026

(54) 3D MICROELECTRODE ARRAYS (3D MEAS) WITH MULTIPLE SENSING CAPABILITIES FOR THE INVESTIGATION OF ELECTROGENIC CELLS

(71) Applicant: University of Central Florida Research Foundation, Inc., Orlando, FL (US)

(72) Inventors: Swaminathan Rajaraman, Winter Park, FL (US); Charles M. Didier, Dunedin, FL (US); Julia Freitas Orrico, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 766 days.

This patent is subject to a terminal disclaimer.

(21) Appl. No.: 18/046,161

(22) Filed: Oct. 13, 2022

(65) Prior Publication Data

US 2023/0129475 A1    Apr. 27, 2023

Related U.S. Application Data

(60) Provisional application No. 63/262,824, filed on Oct. 21, 2021.

(51) Int. Cl.
    *C12M 3/00* (2006.01)
    *C12M 1/12* (2006.01)
    (Continued)

(52) U.S. Cl.
    CPC ............ *C12M 21/08* (2013.01); *C12M 23/16* (2013.01); *C12M 25/02* (2013.01); *C12M 41/12* (2013.01); *C12M 41/46* (2013.01)

(58) Field of Classification Search
    None
    See application file for complete search history.

(56) References Cited

U.S. PATENT DOCUMENTS

2017/0007813 A1 * 1/2017 Negi .................... A61B 5/6868
2021/0394434 A1 12/2021 Rajaraman et al.
(Continued)

OTHER PUBLICATIONS

Cepeda-Torres et al., "3D Microelectrode Arrays (3D MEAs) with PentaModal Sensing Capabilities for the Investigation of Electrogenic Cells", Gulf Coast Undergraduate Research Symposium @Rice University, Oct. 16-17, 2021. See attached documentation "Publications—NanoBioSensors & Systems Laboratory". (Year: 2021).*
(Continued)

*Primary Examiner* — Holly Kipouros
(74) *Attorney, Agent, or Firm* — ALLEN, DYER, DOPPELT + GILCHRIST, P.A.

(57) ABSTRACT

A three-dimensional (3D) microelectrode array device for in vitro electrophysiological applications includes a substrate and micro vias extending from the bottom face to the top face of the substrate. A microneedle at each micro via extends from the bottom face upward beyond the top face and forms a hypodermic microneedle array on the top face. Metallic traces on the bottom face interconnect the hypodermic microneedles to form the 3D microelectrode array. A microheater is positioned on the bottom face of the substrate. Microfluidic ports may be formed at the substrate. Interdigitated electrodes may be formed at the substrate.

12 Claims, 27 Drawing Sheets

(51) Int. Cl.
   *C12M 1/34*        (2006.01)
   *C12M 3/06*        (2006.01)

(56)                    References Cited

U.S. PATENT DOCUMENTS

2024/0110137 A1*   4/2024   Henriques Minas .. C12M 21/08
2025/0101506 A1*   3/2025   Shkolnikov ............ C12Q 1/686

OTHER PUBLICATIONS

Didier et al., SeedEZ Interdigitated Electrodes and Multifunctional Layered Biosensor Composites (MLBCs): A Paradigm Shift in the Development of In Vitro BioMicrosystems, J Microelectromech Syst. Jun. 26, 2020;29(5) (Year: 2020).*

Kundu et al., Multimodal Microfluidic Biosensor With Interdigitated Electrodes (IDE) And Microelectrode Array (MEA) For Bacterial Detection And Identification, Transducers 2019—Eurosensors XXXIII Berlin, Germany, Jun. 23-27, 2019 (Year: 2019).*

Azim et al., "Fabrication and Characterization of a 3D Printed, MicroElectrodes Platform With Functionalized Electrospun Nano-Scaffolds and Spin Coated 3D Insulation Towards Multi-Functional Biosystems," Journal of Microelectromechanical Systems, vol. 28, No. 4; Aug. 2019; pp. 606-618.

Didier et al., "Facile, Packaging Substrate-Agnostic, Microfabrication and Assembly of Scalable 3D Metal Microelectrode Arrays for In Vitro Organ-on-a-Chip and Cellular Disease Modeling," Transducers 2019—Eurosensors XXXIII; Berlin, Germany; Jun. 23-27, 2019; downloaded from IEEE Xplore; pp. 1686-1689.

Didier et al., "Rapid Makerspace Microfabrication and Characterization of 3D Microelectrode Arrays (3D MEAs) for Organ-on-a-Chip Models," Journal of Microelectromechanical Systems; vol. 30, No. 6; Dec. 2021; pp. 853-863.

Didier et al., "Development of In Vitro 2D and 3D Microelectrode Arrays and Their Role in Advancing Biomedical Research," Journal of Micromechanics and Microengineering; 30; 103001; Jul. 3, 2020; pp. 1-28.

Freitas Orrico et al., "Fabrication and Characterization of 3D Microelectrode Arrays (3D MEAs) with Tri-Modal (Electrical, Optical, and Microfluidic) Interrogation of Electrogenic Cell Constructs," Transducers 2021 Virtual Conference; Jun. 20-24, 2021; Downloaded from IEEE Xplore; pp. 767-770.

Kundu et al., "Development of a 3D Printed, Self-Insulated, High-Throughput 3D Microelectrode Array (HT-3DMEA)," Journal of Microelectromechanical Systems; vol. 29, No. 5; Oct. 2020; pp. 1091-1093.

Morales-Carvajal et al., "Makerspace Microfabrication of a Stainless Steel 3D Microneedle Electrode Array (3D Mea) on a Glass Substrate for Simultaneous Optical and Electrical Probing of Electrogenic Cells," The Royal Society of Chemistry; 10; 2020; pp. 41577-41587.

U.S. Appl. No. 17/805,478, filed Jun. 6, 2022 Inventors: Swaminathan Rajaraman et al.

* cited by examiner

MICROHEATER
PLACEMENT IN
RASTER REGION

FINAL
MICROFABRICATED
PENTA-MODAL 3D
MEA (C)

| EQUIVALENT CIRCUIT PARAMETERS | |
| --- | --- |
| EQUATION PARAMETER | NUMERICAL VALUE |
| $R_1$ | 697.3 (Ω) |
| $R_2$ | 64.458 (Ω) |
| $Q_1$ | $5.145 \times 10^{-7}$ ($\Omega^{-1} \cdot s^{n}$) [44] |
| $n_1$ | 0.71534 |
| $W_{sr1}$ | $3.0 \times 10^{5}$ ($\Omega \cdot s^{-0.5}$) [33,44] |
| $W_{sc1}$ | 0.21358 ($s^{0.5}$) [33,44] |

| EQUIVALENT CIRCUIT PARAMETERS | | | | | |
|---|---|---|---|---|---|
| EQUATION PARAMETER | NUMERICAL VALUE | | | | |
| | 22C | 27C | 32C | 37C | 42C |
| $R_{1*}$ | 6.9556 ($\Omega$) | 7.7416 ($\Omega$) | 15.001 ($\Omega$) | 1.592 ($\Omega$) | 1.3317 ($\Omega$) |
| $R_{2*}$ | 107.05 ($\Omega$) | 98.113 ($\Omega$) | 94.408 ($\Omega$) | 93.166 ($\Omega$) | 87.963 ($\Omega$) |
| $R_3$ | 171.98 ($\Omega$) | 158.03 ($\Omega$) | 137.6 ($\Omega$) | 150 ($\Omega$) | 144.49 ($\Omega$) |
| $C_1$ | 5.6135 ($\mu$F) | 1.0802 ($\mu$F) | 1.7704 ($\mu$F) | 1.7927 ($\mu$F) | 2.2932 ($\mu$F) |
| $Q_1$ | $4.6722 \times 10^{-11}$ ($\Omega^{-1} \cdot s^n$) | $4.5721 \times 10^{-11}$ ($\Omega^{-1} \cdot s^n$) | $4.7008 \times 10^{-11}$ ($\Omega^{-1} \cdot s^n$) | $3.9271 \times 10^{-11}$ ($\Omega^{-1} \cdot s^n$) | $3.7798 \times 10^{-11}$ ($\Omega^{-1} \cdot s^n$) |
| $n_1$ | 1 | 1 | 1 | 1 | 1 |
| $W_{or1}$ | 2717.6 ($\Omega \cdot s^{-0.5}$) | 5763.6 ($\Omega \cdot s^{-0.5}$) | 7404.6 ($\Omega \cdot s^{-0.5}$) | 7448 ($\Omega \cdot s^{-0.5}$) | 7961 ($\Omega \cdot s^{-0.5}$) |
| $W_{oc1}$ | 0.15667 ($s^{0.5}$) | 0.38313 ($s^{0.5}$) | 0.39796 ($s^{0.5}$) | 0.38312 ($s^{0.5}$) | 0.38313 ($s^{0.5}$) |

EXTRACTED EQUIVALENT CIRCUIT PARAMETERS FROM TEMPERATURE SENSING IDE.

FIG. 4G

| EQUIVALENT CIRCUIT PARAMETERS | | | | | |
|---|---|---|---|---|---|
| EQUATION PARAMETER | NUMERICAL VALUE | | | | |
| | PLAIN IDE* | ANTIBODY | 0.2mM L-GLUT | 2mM L-GLUT | 20mM L-GLUT |
| $R_1$** | $1.613 \times 10^{-15}$ ($\Omega$) | 18.511 ($\Omega$) | 15.699 ($\Omega$) | 25.966 ($\Omega$) | 26.816 ($\Omega$) |
| $R_2$** | 28.558 ($\Omega$) | 226.06 ($\Omega$) | 259.77 ($\Omega$) | 208.23 ($\Omega$) | 195.04 ($\Omega$) |
| $R_3$ | 130.71 ($\Omega$) | 125.93 ($\Omega$) | 137.64 ($\Omega$) | 160.29 ($\Omega$) | 168.86 ($\Omega$) |
| $R_4$ | N/A | 223.13 ($\Omega$) | 277.81 ($\Omega$) | 255.12 ($\Omega$) | $1.5247 \times 10^{-12}$ ($\Omega$) |
| $C_1$ | 8.5097 ($\mu$F) | N/A | N/A | N/A | N/A |
| $Q_1$ | $5.1953 \times 10^{-11}$ ($\Omega^{-1} \cdot s^n$) | $2.209 \times 10^{-06}$ ($\Omega^{-1} \cdot s^n$) | $2.7328 \times 10^{-06}$ ($\Omega^{-1} \cdot s^n$) | $2.1815 \times 10^{-06}$ ($\Omega^{-1} \cdot s^n$) | $1.346 \times 10^{-05}$ ($\Omega^{-1} \cdot s^n$) |
| $n_1$ | 0.98124 | 0.98929 | 0.99848 | 1 | 0.53362 |
| $Q_2$ | N/A | $2.9301 \times 10^{-10}$ ($\Omega^{-1} \cdot s^n$) | $9.908 \times 10^{-11}$ ($\Omega^{-1} \cdot s^n$) | $8.5813 \times 10^{-11}$ ($\Omega^{-1} \cdot s^n$) | $7.8265 \times 10^{-11}$ ($\Omega^{-1} \cdot s^n$) |
| $n_2$ | N/A | 0.917 | 0.97701 | 1 | 1 |
| $Q_3$ | N/A | $1.2463 \times 10^{-07}$ ($\Omega^{-1} \cdot s^n$) | $1.0646 \times 10^{-06}$ ($\Omega^{-1} \cdot s^n$) | $5.4109 \times 10^{-07}$ ($\Omega^{-1} \cdot s^n$) | $1.218 \times 10^{-04}$ ($\Omega^{-1} \cdot s^n$) |
| $n_3$ | N/A | 0.86371 | 0.69896 | 0.75971 | $3.706 \times 10^{-07}$ |
| $W_{or1}$ | 1848.4 ($\Omega \cdot s^{-0.5}$) | 8633.7 ($\Omega \cdot s^{-0.5}$) | 10991 ($\Omega \cdot s^{-0.5}$) | 7990.3 ($\Omega \cdot s^{-0.5}$) | 11401 ($\Omega \cdot s^{-0.5}$) |
| $W_{oc1}$ | 0.1394 ($s^{0.5}$) | 0.4294 ($s^{0.5}$) | 0.44603 ($s^{0.5}$) | 0.38313 ($s^{0.5}$) | 0.12731 ($s^{0.5}$) |

EXTRACTED EQUIVALENT CIRCUIT PARAMETERS FROM ANALYTE SENSING IDE.

3D MICROELECTRODE ARRAYS (3D MEAS) WITH MULTIPLE SENSING CAPABILITIES FOR THE INVESTIGATION OF ELECTROGENIC CELLS

GOVERNMENT SPONSORSHIP

This project is currently supported by National Science Foundation REU Site EEC 2050266, National Institute of Health (NIH) UG3TR003150, and associated with the University of Central Florida Account No. 63018A43.

PRIORITY APPLICATION(S)

This application is based upon U.S. provisional patent application Ser. No. 63/262,824 filed Oct. 21, 2021, the disclosure which is hereby incorporated by reference in its entirety.

FIELD OF THE INVENTION

The present invention relates to the field of microelectrode arrays, and more particularly, this invention relates to three-dimensional (3D) microelectrode arrays (MEAs) with electrophysiological and multiple sensing capabilities.

BACKGROUND OF THE INVENTION

In vitro organ-on-a-chip models are a recently emerging technology that is built at the intersection of micro/nano-engineering and cellular biology. These hybrid innovations aim to simulate physiology at the tissue and organ level by developing them concurrently with interfaced technology. Further sophistication of such organ-on-a-chip models requires careful crafting of organoids, spheroids, and multi-aggregate cellular models, to better replicate the body's systems in vitro. Such tissue cultures have been developed for benchtop investigation and historically have proven to provide major breakthroughs in biological research. However, these more complex cellular models also demand multiplexed systems and strategies to procure multifarious data sets over long-term integration with these models of increasing complexity.

Three-dimensional (3D) microelectrode arrays (3D MEAs) have been developed as a next generation tool. 3D MEAs are an arrangement of microelectrodes in defined patterns that transduce voltage and current signals from electrically active cells and cellular constructs, to provide readily available, functional metrics for assessing cellular health, proliferation, and activity (either spontaneous or elicited). Due to this ubiquitously applied nature, 3D MEAs have often formed the base sensing and stimulation platform on to which other sensing modalities may be integrated.

Recently, alternative fabrication strategies have been employed in the fabrication of 3D MEA biosensors. These unique approaches host a multitude of benefits from a functional device perspective, including easily interchangeable additive and subtractive fabrication methods, and the integration of substrate materials for optical clarity, which is crucial for transmitted light imaging. Transparency is desired in such benchtop devices to provide standard observational methods for comparative analysis of specialized sensing techniques. Therefore, transparent polymer substrates are possible candidates where combinatorial additive and subtractive microfabrication steps are readily integrated. It may be desirable to increase the collection of data from a single platform using similar readout methodologies, such as impedimetric frequency sweeps. Electrode configurations for such measurements may increase sensitivity and use in sensing multiple signatures, such as temperature and key-analyte concentration monitoring, which for the intended cellular biosensing applications, may be desirable.

SUMMARY OF THE INVENTION

This summary is provided to introduce a selection of concepts that are further described below in the Detailed Description. This summary is not intended to identify key or essential features of the claimed subject matter, nor is it intended to be used as an aid in limiting the scope of the claimed subject matter.

In general, a three-dimensional (3D) microelectrode array (MEA) device for in vitro electrophysiological applications may comprise a substrate having a top face and opposing bottom face. A plurality of micro vias may be formed within the substrate and extend from the bottom face to the top face. A microneedle at each micro via may extend from the bottom face upward beyond the top face and form a hypodermic microneedle array on the top face. Metallic traces may be formed on the bottom face and interconnect the hypodermic microneedles to form the 3D microelectrode array. A microheater may be positioned on the bottom face of the substrate. Microfluidic ports may be formed at the substrate.

A temperature sensing electrode may be formed on the top face adjacent the microheater positioned on the bottom face. An analyte sensing electrode may be formed on the top face adjacent the 3D microneedle array. The substrate may comprise at least one polymer selected from the group consisting of: Polycarbonate, Polystyrene, Poly(methyl), Cyclic olefin copolymer, Cyclic olefin polymer, Polyethylene terephtalate, Polyethylene terephthalate glycol, and Polysulfone. The substrate may be about 100 μm to 5.0 mm in thickness. A culturing area may be formed in the top face and may comprise a ring of transparent polymer. The ring of transparent polymer may comprise at least one polymer selected from the group consisting of: Polycarbonate, Polystyrene, Poly(methyl methacrylate), Cyclic olefin copolymer, Cyclic olefin polymer, Polyethylene terephthalate, Polyethylene terephthalate glycol, and Polysulfone. A cutout may be formed on the underside of the substrate into which the microheater is positioned. The cutout may be about 100 micrometers square up to about 10 millimeters square.

In yet another example, a three-dimensional (3D) microelectrode array device for in vitro electrophysiological applications may comprise a substrate having a top face and opposing bottom face. A plurality of micro vias may be formed within the substrate and extend from the bottom face to the top face. A microneedle at each micro via may extend from the bottom face upward beyond the top face and form a hypodermic microneedle array on the top face. Metallic traces may be formed on the bottom face and interconnect the hypodermic microneedles to form the 3D microelectrode array. A microheater may be positioned on the bottom face of the substrate. A temperature sensing interdigitated electrode may be formed on the top face adjacent the microheater positioned on the bottom face. An analyte sensing interdigitated electrode may be formed on the top face adjacent the 3D microneedle array. Microfluidic ports may be formed at the substrate. A culturing area may be formed in the top face.

Each of the temperature sensing and analyte sensing interdigitated electrodes may comprise a two-finger circle-in-line configuration, and each finger may comprise a plurality of metallic contacts forming the electrode in the circle-in-line configuration. The analyte sensing interdigitated electrode may include a gold layer interface for antibody adherence. The analyte sensing interdigitated electrode may comprise one or more attached antibodies.

A method of forming a three-dimensional (3D) microelectrode array device for in vitro electrophysiological applications may comprise forming a substrate having a top face and opposing bottom face, and forming a plurality of micro vias within the substrate and extending from the bottom face to the top face. The method further includes inserting a microneedle within each micro via to extend upward from the bottom face beyond the top face to form a hypodermic microneedle array on the top face, forming metallic traces on the bottom face and interconnecting the hypodermic microneedles to form the 3D microelectrode array, and forming a microheater positioned on the bottom face of the substrate. Interdigitated electrodes may be formed at the substrate. Microfluidic ports may be formed at the substrate.

BRIEF DESCRIPTION OF THE DRAWINGS

Other objects, features and advantages of the present invention will become apparent from the Detailed Description of the invention which follows, when considered in light of the accompanying drawings in which:

FIG. 4A shows a compilation of impedimetric temperature recordings across the (22° C.-42° C.) temperature range with 1° C. increments.

FIG. 4B is a graph showing selected temperatures (every 5° C.) from FIG. 4A and additionally including fitted models for each, derived from an equivalent circuit shown as an inset.

FIG. 4C is a graph showing enhanced inset data from FIG. 4B showing the 1 MHz to 4 MHz region of interest where changes in the faradaic reactions at the electrode surface are apparent and showing a clear decreasing impedance trend, consistent with a hypothesis of increased kinetic activity within the electrolyte solution.

FIG. 4D is a graph of a Nyquist plot variation of the data from FIGS. 4B and 4C, which plots imaginary impedance against real impedance and where the curve corresponds to the first faradaic reactions governed by the start of the equivalent circuit, present at the higher frequencies as indicated and the highlighted region of the curve is governed primarily by $R1^*$ and $R2^*$ and confirms the same trend of decreasing real impedance observed in the graph of FIG. 4C.

FIG. 4E shows a full Nyquist plot for the fitted and experimental results for the selected temperatures, and where the inset includes the equivalent circuit for the reference.

FIG. 4F is a graph showing a full spectrum phase plot for all temperatures.

FIG. 4G is a table showing extracted equivalent circuit parameters from the temperature sensing IDE.

FIG. 5A is a graph of the compilation of all impedimetric temperature recordings from the various states of the analyte IDE.

FIG. 5B is a graph of the impedance data from FIG. 5A that includes fitted models for each state, derived from the equivalent circuit shown as an inset where the "plain" IDE state was fitted using the equivalent circuit from FIG. 4B.

FIG. 5C is a graph for the enhanced data from FIG. 5B showing the 1 MHz to 4 MHz region of interest, where changes in the faradaic reactions at the electrode surface are apparent, and as opposed to the temperature sensor, a clear increasing impedance trend is observed.

FIG. 5D is a graph of the Nyquist plot variation of the data from FIGS. 5B and 5C, which plots imaginary impedance against real impedance, and where the curve corresponds to the first faradaic reactions governed by the start of the equivalent circuit, present at the higher frequencies and the curve is governed by R1, R2, and CPE1** and confirms the increase in real impedance as observed in FIG. 5C, where additionally, a change in the curve shape is observed, owing to the capacitive elements imposed on the IDE surface from antibody conjugation and analyte binding.

FIG. 5E is a scanning electron microscopy (SEM) image of the Ti/Au IDE on the substrate surface along with the 3D microelectrode array.

FIG. 5F is a SEM image of the IDE with a higher magnification showing the conjugated antibodies on the surface.

FIG. 5G is an AFM image and schematic illustration of the image from FIG. 5F where the first image (i) indicates the functional Au IDE surface before antibodies are added, image (ii) indicates the surface of the IDE after antibody conjugation, and image (iii) is a schematic illustration serving to show the overall fabrication of the IDE sensor on the substrate, followed by a mixed air plasma treatment, Ti seed layer, Au functional layer, and then antibody conjugation facilitated by another mixed air plasma treatment.

FIG. 5J is a table showing the extracted equivalent circuit parameters from the analyte sensing IDE.

FIG. 6A shows an optical imaging of the C2C12 myocytes.

FIG. 6B is an image of calcein AM, live staining of the cells.

FIG. 6C is an image showing propidium Iodide stain for live/dead cell confirmation.

DETAILED DESCRIPTION

Figures 1A, 1B, 1C:
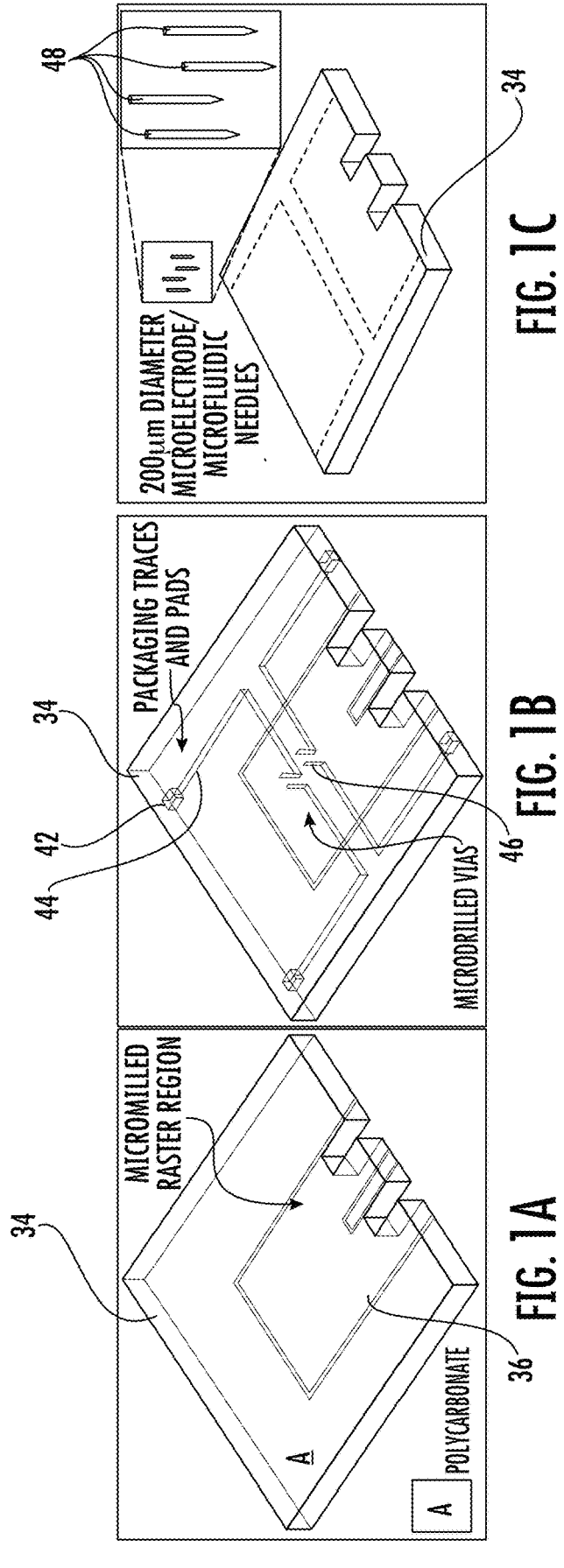
FIG. 1A is a schematic drawing of a first step in the process flow for the fabrication of the multi-modal biosensor as the 3D MEA device, and shows a micromilled bulk polycarbonate (PC) base having a raster-region with a thin cut-out where the microheater is to be placed.
FIG. 1B is a drawing showing the micromilling and microdrilling of packaging traces, pads, and through-vias respectively.
FIG. 1C is a drawing showing magnetic-assisted insertion of microneedles to define the bulk 3D MEA structure.

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

Previous work on microelectrode arrays (MEAs) is expanded by developing and demonstrating temperature and analyte sensing built on thin film interdigitated electrodes (IDEs) and using detailed impedimetric characterization. To properly modulate and sense temperatures, a microheater was integrated into the single chip design for the 3D MEA device and is used in the characterization of the temperature sensor's performance. For analyte analysis, a simple conjugation regimen was developed, and anti-L-Glutamine antibodies were used for sample detection. Because all electrical sensing modalities use impedance spectroscopy for data output, the software identified differences in the equivalent circuits and extract resultant parameters. For temperature and analyte sensors, Nyquist plots were employed to characterize their sensing performances.

The three-dimensional (3D) microelectrodes were characterized by employing Root Mean Square (RMS) noise levels that are acceptable for electrophysiology. The optical transparency of the platform was demonstrated for biocompatibility imaging of C2C12 myocytes. A COMSOL finite element modelling of fluid flow through any microfluidic ports demonstrated precise perfusion capabilities in a localized area. Together, these five modalities enabled multisensing as a penta-modal, polymer-metal biosensor platform for comprehensive MPS analytics encompassing: 1) electrophysiology, 2) temperature sensing, 3) analyte sensing, 4) transparency-mediated imaging, and 5) microfluidic perfusion.

Benchtop tissue cultures have become increasingly complex in recent years, as organ-on-a-chip and Microphysiological Systems (MPS) incorporate cellular constructs that more accurately represent their respective biological systems. These systems provide major breakthroughs in biological research and may shape the field in the coming decade. These biological systems may require integrated sensing/stimulation modalities to produce complex, multiplexed datasets, with enhanced combinatorial biological detail, which may be required for evaluation of in vitro electrogenic systems seamlessly in the same platform. A polymer-metal based 3D MEA device is illustrated generally at 30 (FIG. 1J) as the final MEA device, in accordance with a non-limiting example, and operates as a compound biosensor that encompasses five total modalities for sensing/ stimulation, including: 1) electrical/electrochemical, 2) optical, 3) microfluidics, 4) temperature, and 5) analyte-sensing, thus providing a penta-modal sensing platform designed for electrogenic cellular constructs and allowing comprehensive MPS data collection.

The 3D MEA device 30 development process is shown schematically in the sequence of FIGS. 1A-1J. It was possible to use Solidworks 3D design software (Dassault Systèmes, France), and in an example, a 24 mm×24 mm Polycarbonate (PC) substrate 34 was used for chip and designed and micromilled from a 1.75 mm bulk substrate. The substrate 34 may be formed as a polymer selected from the group consisting of: Polycarbonate, Polystyrene, Poly (methyl methacrylate), Cyclic olefin copolymer, Cyclic olefin polymer, Polyethylene terephthalate, Polyethylene terephthalate glycol, and Polysulfone.

Figure 1E:
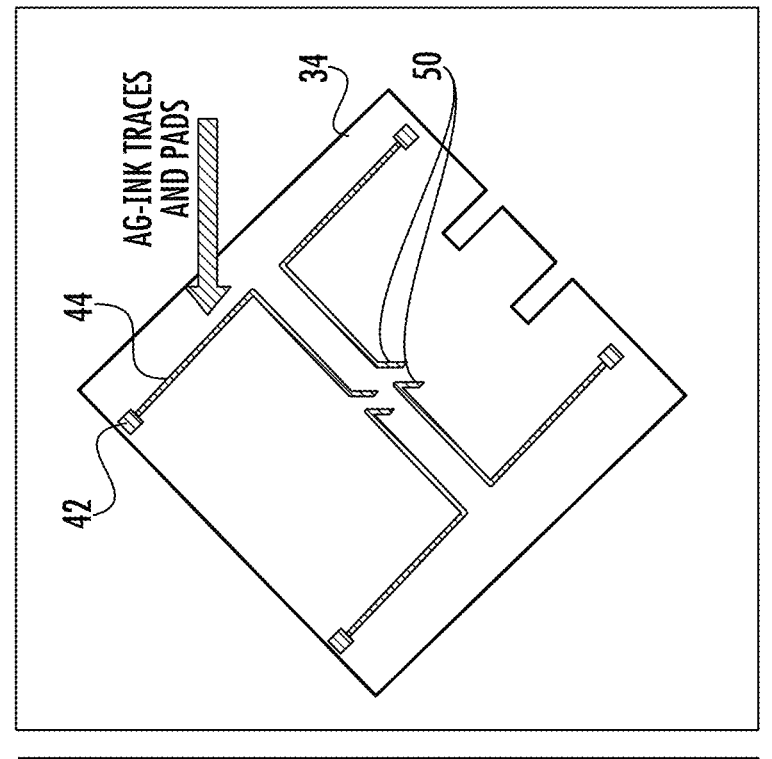
FIG. 1E is a drawing showing the final cured Ag-ink, defining the functional packaging for the 3D MEA sensing modality.
Figure 1D:
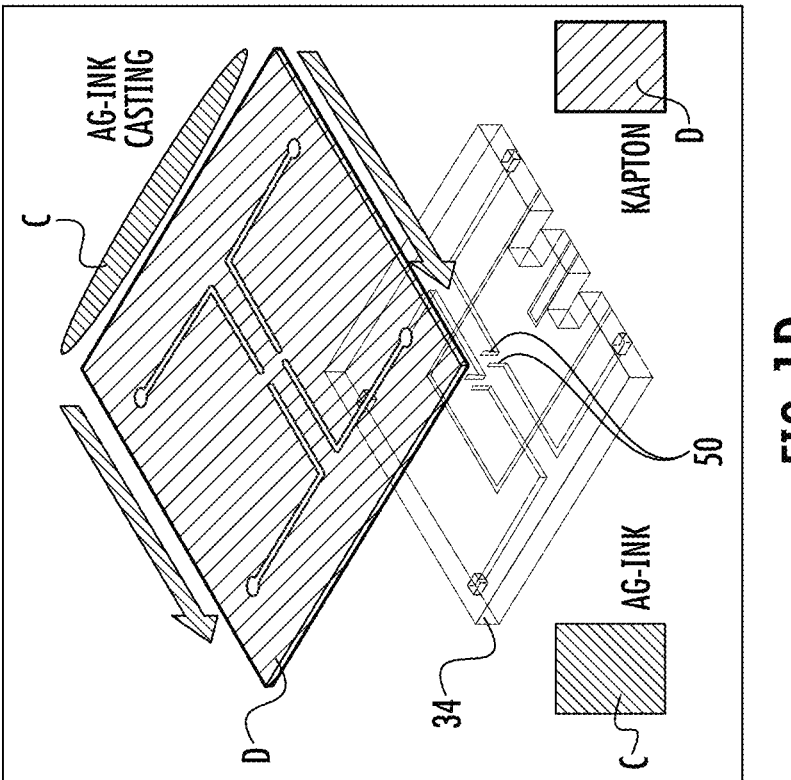
FIG. 1D is a drawing showing precision silver (Ag)-ink casting of the traces, pads and vias from FIG. 1C, using a laser micro-machined Kapton® mask.

In this example, Drawing Interchange Format (DXF) files from the 3D design were imported into a T-Tech QC-J5 Quick Circuit Prototyping Systems (T-Tech, USA) for micro-drilling (μD) and micromilling. A cutout 36 as a raster pattern of about 100 μm×100 μm (L×W) and having a depth of 300 μm was micromilled on the back of the substrate 34, and into the position where a microheater 40 was later placed (FIG. 1I). It is possible that the cutout 36 may be about 100 micrometers square up to about 10 millimeters square. Subsequently, 1 mm×1 mm contact pads 42 were micromilled with 200 μm wide traces 44 to define packaging components on the backside of the substrate (FIG. 1B). Additionally, 220 μm wide and 500 μm deep vias 46 were microdrilled (μD) in the center of the substrate 34 to place 3D microneedles 48 for 3D microelectrodes definition (FIGS. 1B and 1C). It is possible that the substrate 34 may be about 100 μm to about 5.0 mm in thickness.

3D microelectrode structures were defined using about 200 μm diameter microneedles 48 (DBCTM, South Korea). Using a 1064 nm IR wavelength, the microneedles 48 were laser micromachined (QuikLaze, USA) and then subsequently clipped to a final height of about 1.85 mm. The 3D microelectrodes from the microneedles 48 were manually placed using a magnetic insertion process (MagIN) shown in FIG. 1C, leaving a functional height of the final microelectrode of approximately 100 μm. The 3D microelectrodes 50 were packaged using conductive silver (Ag)-ink (EP3HTSMED; MasterBond, USA) casting, which was defined atop the micromilled traces 44 and contact pads 42 on the backside of the substrate 34 as the chip. UV-laser micromachined Kapton® (DuPont, USA) shadow masks were utilized to aid the process and ensure high specificity in definition. The Ag-ink was cured at 60° C. for 24 hours to achieve a mechanically robust profile (FIGS. 1D and 1E).

Figures 1F, 1G, 1H:
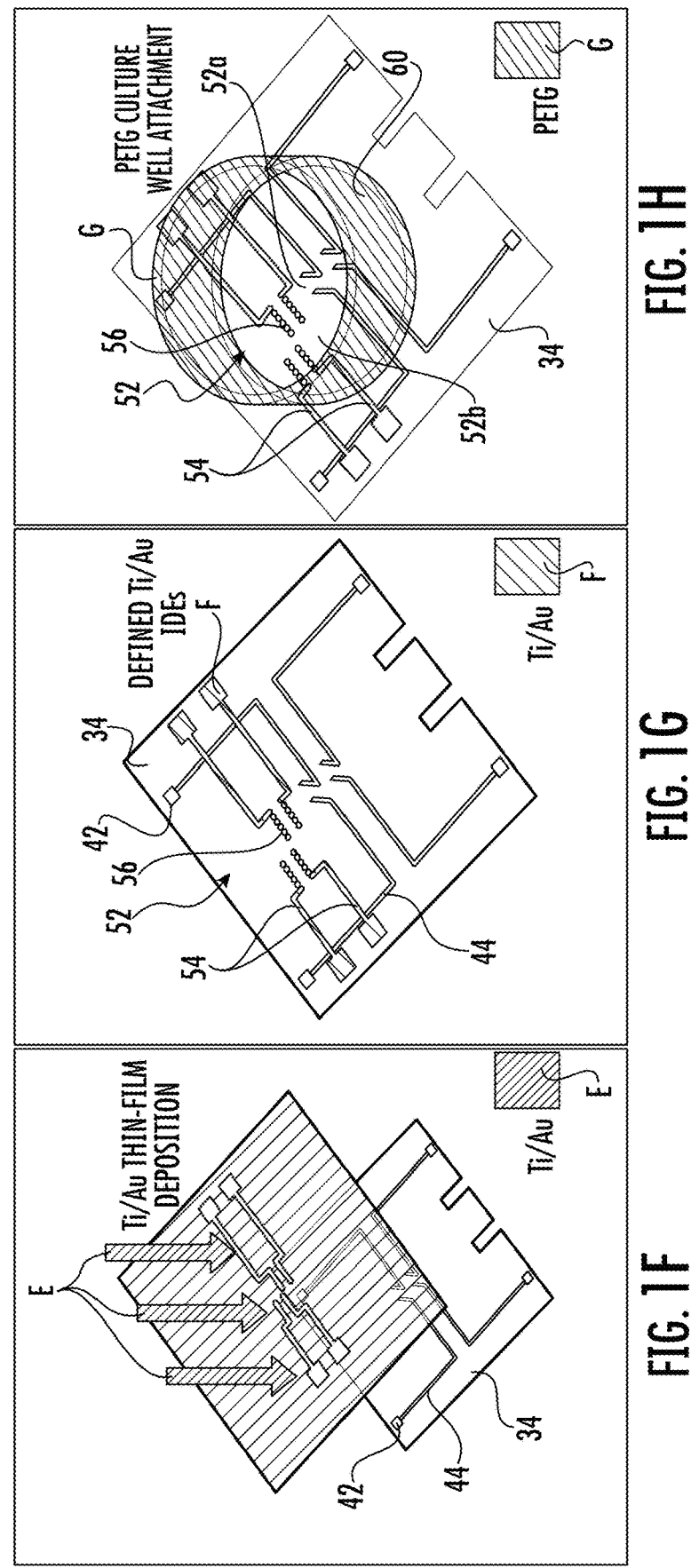
FIG. 1F is a drawing showing thin-film, electron beam deposition of Titanium (Ti)/Gold (Au) IDEs and contact pads for the temperature and analyte-sensing modalities.
FIG. 1G is a drawing showing final defined IDEs on the top surface of the polycarbonate substrate.
FIG. 1H is a drawing showing PET-G culture well attachment with 10:1 polydimethylsiloxane (PDMS).
Figure 1I:
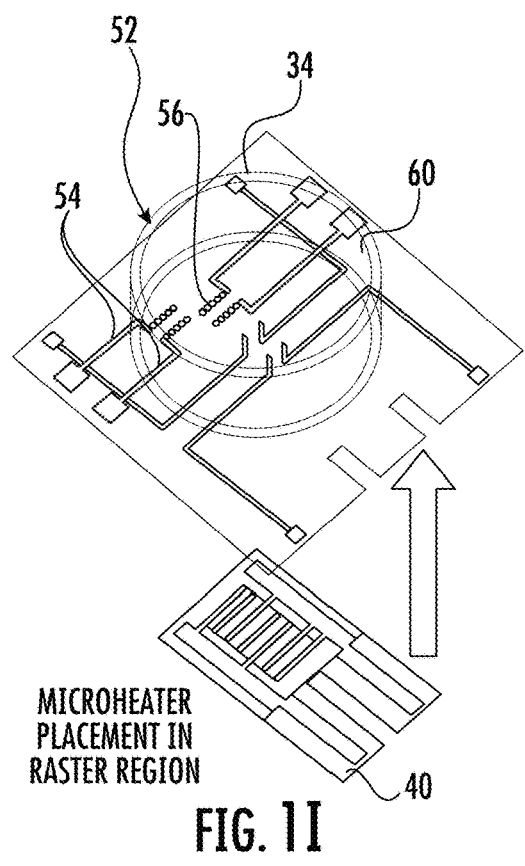
FIG. 1I is a drawing showing microheater placement into the raster-region on the underside of the substrate.

Shadow masks were designed using Solidworks 3D CAD software and were UV-laser micro-machined from 25 μm thick Kapton® sheets, with a biocompatible adhesive backing layer (FIG. 1F). Titanium (Ti)-Gold (Au) Interdigitated Electrodes (IDEs) 52 were defined with overall dimensions having a two-finger, 750 μm pitch circle-in-line geometry. Each finger 54 included five (5) 750 μm diameter, contiguous circles or contacts 56 and resulted in a total functional length of 3.75 mm. Masks were subsequently aligned utilizing existing features on the top-side of the chips.

The temperature sensing IDE mask was placed adjacent to, but not directly on top of the location of microheater 40 underneath the substrate 34 chip. All temperature sensing IDEs were fabricated using Electron-beam (E-beam) evaporation (100 nm Ti/200 nm Au; Thermionics, USA).

The analyte sensing IDE mask was placed adjacent to the 3D microelectrodes 48 (FIG. 1G). Analyte sensing IDEs were defined with the same Ti/Au e-beam as described above using known Au layers to serve as the functional interface for antibody adherence, vial Thiol-mediated adsorption. Anti-L-Glutamine specific antibodies (Abcam, UK) were obtained (about 10 mg/ml) and were subsequently diluted down to about 0.1 mg/ml (100:1) aliquots in Dulbecco's Phosphate Buffered Saline (DPBS; Millipore Sigma, USA). The devices were washed with 70% Ethanol (Sigma Aldrich, USA), dried and then plasma treated (Plasma Etch, USA) for 20 seconds under mixed air conditions. A measured volume of 40 μl of the diluted antibody aliquot was pipetted onto the plasma-treated Au-IDE surfaces, and incubated at 22° C. for one hour before being gently washed with deionized (DI) water and drying.

A culture well 60 was defined using a transparent Polyethylene terephthalate glycol (PETG) ring, with about 16 mm inner diameter, and about 8 mm height as shown in FIG. 1H. Standard 10:1 polydimethylsiloxane (PDMS) viscoelastic polymer was used to attach the culture well and was allowed to cure at about 60° C. for about two hours to achieve its final properties. The culture well 60 may include a ring of transparent polymer that comprises at least one polymer selected from the group consisting of: Polycarbonate, Polystyrene, Poly(methyl methacrylate), Cyclic olefin copolymer, Cyclic olefin polymer, Polyethylene terephthalate, Polyethylene terephthalate glycol, and Polysulfone.

It is possible the culture well 60 may include a plurality of microneedles, e.g., about 2 to about 64 microelectrodes. The length of the microneedles 48 may be about 1.3 to about 1.6 times greater than the thickness of the substrate 34. The height of the microneedle array extending above the top face of the substrate may be about 25 μm to about 5 mm.

Figure 1J:
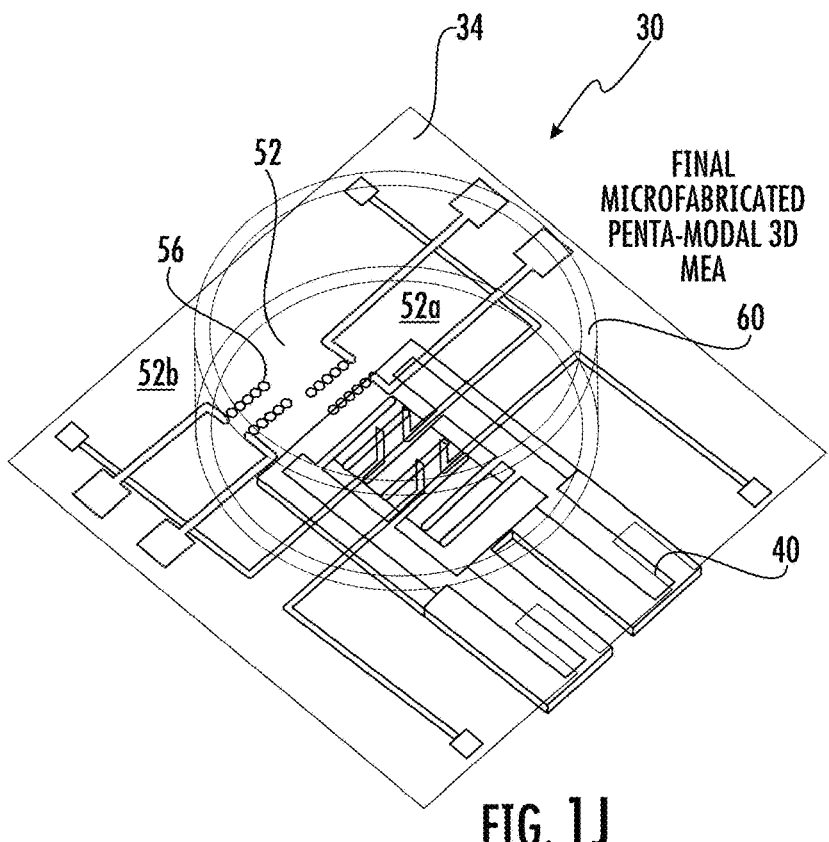
FIG. 1J is a drawing showing a final fabricated Penta-Modal (multiple sensing) 3D MEA biosensor platform as the 3D MEA device.

The resistive microheater 40 (Pelonis Technologies, USA) was attached to the backside of the substrate 34 as the chip in the micromilled raster region for the cutout 36 as shown in FIGS. 1I-1J. To use the microheater 40, the cathode and anode connections were wire-bonded to contact points. The microheater 40 was powered with a source meter (Keithley, USA), holding the current compliance at 1.05 μA and varying the voltage from 0.5V-7V (with 0.5V increments). To measure the resulting temperatures and calibrate the microheater 40, a combination of an infrared thermal camera (Perfect Prime, USA) and an external probe were used.

Full spectrum impedance and phase characterization were obtained with electrochemical impedance spectroscopy (EIS) on a Bode 100 impedance measurement system (Omicron Labs, Austria). Measurements were performed across the frequency range of 10 Hz to 40 MHz in DPBS (Dulbecco's phosphate-buffered saline) with a Platinum (Pt) counter electrode. Root Mean Square (RMS) noise measurements were obtained using a MUSE® electrophysiology system (Axion BioSystems, USA).

The interdigitated electrode 52 characterization was obtained using either a single IDE finger 54 with a Pt counter electrode in DPBS as was used in the 3D microelectrodes 50 characterization protocol or between both fingers of the respective IDE. Scans were obtained across a full frequency spectrum of 10 Hz to 40 MHz.

For temperature sensing IDEs 52a, both fingers were used to measure changes in DPBS. Baseline impedance spectra were recorded at 22° C. corresponding closely with room temperature. Impedance scans were subsequently recorded as voltage was increased from 0.5V-7V across the microheater to produce a range of physiologically relevant temperature ranges from 22° C. to 42° C. Changes in impedance were recorded as the temperature increased. Temperatures were validated using the IR thermal camera and with an additional external probe.

IDE 52 impedance measurements were obtained in the same manner as the temperature sensing IDE measurements. However, the measurements were made using a single finger 54 of the IDE 52 coupled with a Pt counter electrode. To provide baseline recordings, bare sensors were characterized before conjugating the antibodies as described previously.

Impedance measurements were then obtained again on the conjugated IDEs 52 to assess the sensitivity of each step in the process. As an indirect measure of the surface modification of the IDEs 52, aliquots of L-Glutamine were created at varying concentrations in DPBS (20 mM, 2 mM, and 0.2 mM). Between each scan and when changing concentration, sensors were washed with fresh DPBS for 30 s to allow the IDEs 52 to recalibrate.

Fitting analysis of the 3D microelectrodes 50, temperature IDEs 52a, and analyte IDEs 52b was performed using the EIS Spectrum Analyser Software (EIS Spectrum Analyser Software, Belarus), using 300 iterations for convergence of the Powell algorithm, while employing the amplitude function.

Samples were imaged using a combination of atomic force microscopy (AFM) and scanning electron microscopy (SEM) imaging. The AFM (Veeco dimension 3100, USA) was used in the tapping mode with PR-EX-T125-10 tips (Resonant Frequency, 200-400 kHz; Spring Constant, 13-77 N/m; Anasys Instruments, USA). Scanning electron microscopy (SEM) (Zeiss 40, Germany) imaging was performed at an incident voltage between 1-5 keV. Optical images were obtained using an iPhone XS (Apple, USA). Fluorescence and optical microscopy were obtained using the Keyence BZ-X810, laser confocal microscope (Keyence, Japan). The laser confocal excitation wavelengths of the system were 470 nm+/−40 (Calcein AM) and 560 nm+/−40 (Propidium Iodide).

COMSOL modelling of localized microfluidic flow ingress into the culture well 60 (total volume of 1,608.5 mm3), was modelled using a time-dependent, laminar flow arrangement (COMSOL Multiphysics 5.4; COMSOL Inc., Sweden). The model was calculated using the finer mesh setting. The model itself was calculated as a 2D representation of the 3D fluid space to better visualize the ingress of microfluidic volumes. The fluidic ports used in this model, were dimensioned similar to 30 G dispensing needles (BS-TEANTM, USA), in two-dimensional equivalent (OD: 220 μm; ID: 160 μm). The pressure applied was a nominal 8 Pa (Pascal) of force to simulate a gentle press on a syringe, which provides more control based on maximal human-applied syringe pressures. The liquid injected was simulated using the 0.2 mM L-Glutamine solution.

C2C12 murine myoblast cells (CRL-1772™; ATCC, USA) were cultured using a standard protocol on the penta-modal devices for 5 days in vitro (DIV). Brightfield and fluorescence microscopy were performed as with the procedure described above using Calcein AM and Propidium Iodide live/dead stains (Thermo Fisher Scientific, USA) for transparency and transmittance confirmation, as well as for cellular viability calculations.

Figures 2A, 2B, 2C, 2D, 2E, 2F:
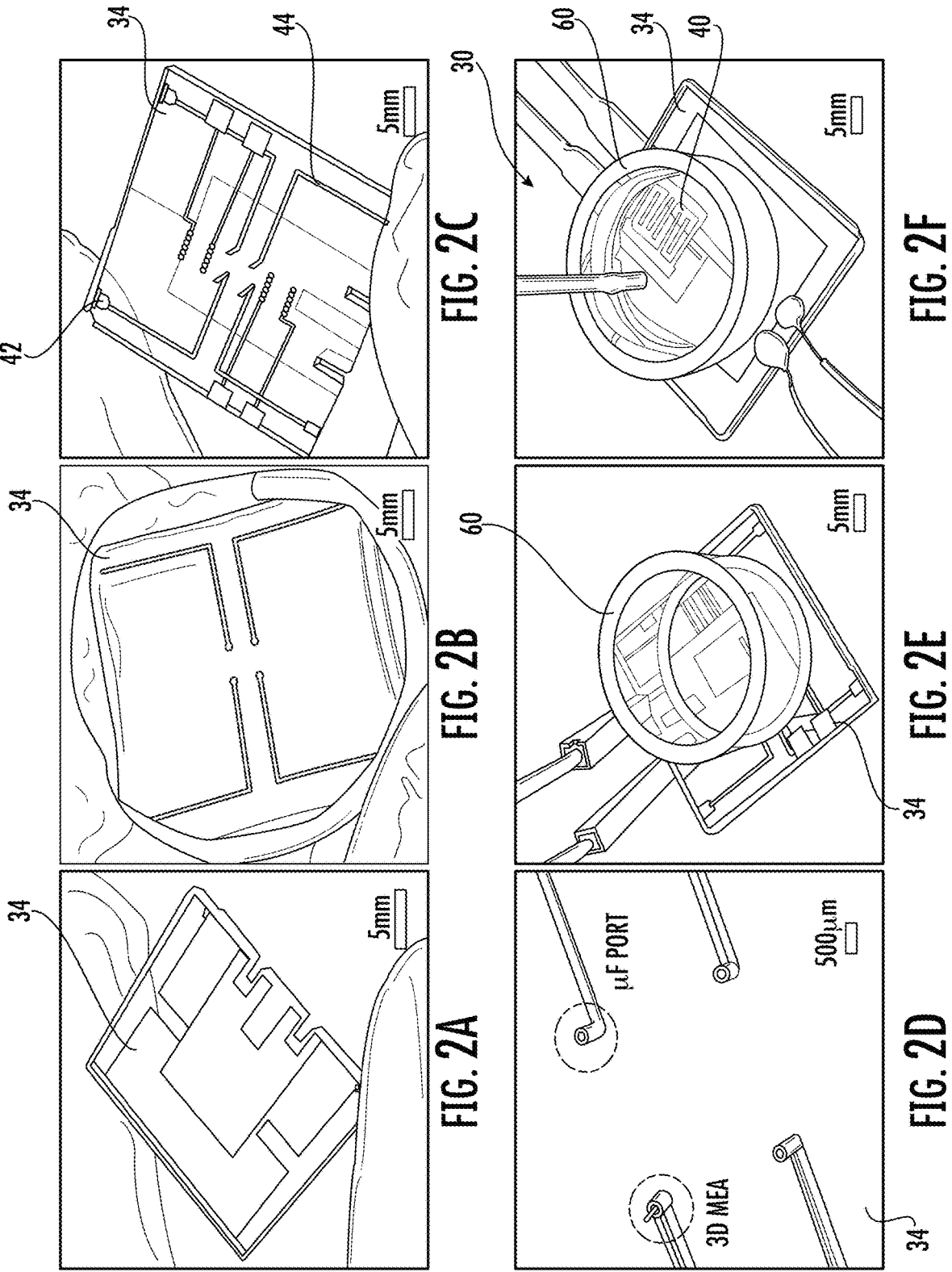
FIG. 2A is an optical image showing a first microfabrication stage of the 3D microelectrode array device as a multi-modal biosensor described in FIGS. 1A-1J, and showing an optical image corresponding to FIG. 1B where the protective film is left partially in place to better contrast each micromilled, microdrilled, or micro-rastered element.
FIG. 2B is an optical image corresponding to FIG. 1E where the cured Ag-ink is precision aligned to reside within the desired packaging traces and pads.
FIG. 2C is an optical image corresponding to FIG. 1G where both Ti/Au interdigitated electrodes (IDEs) for the thermal and analyte sensor have been deposited, and inkcast tracing leading to the 3D microelectrode arrays can be observed, along with the micro-rastered microheater region.
FIG. 2D is a close-up optical image of the central device region from FIG. 2C where microfluidic (µF) ports may be substituted or added to the 3D microelectrode insertion vias, and additional microfluidic ports may be added elsewhere in the culturing area.
FIG. 2E is an optical image of the culture well as attached.
FIG. 2F is an optical image of the 3D microelectrode array device as a fabricated biosensor from FIG. 1J, showing the microheater attached in the micro-rastered region for testing the temperature sensing capabilities.

FIGS. 1J and 2F show the fully fabricated 3D MEA device 30 encompassing the five sensing modalities identified above. The final penta-modality of the 3D MEA device 30 included: 1) optical clarity for image-based analysis, 2) microfluidics (μF), 3) electrophysiology (3D MEA), 4) temperature sensing, and 5) analyte (L-Glutamine) sensing and were demonstrated in a single device. The images of FIGS. 2A-2F illustrate the different stages of the 3D MEA device 30 microfabrication.

It was desirable to create the 3D MEA device 30 with temperature regulation capabilities as assays performed within the group and many others take place outside of a cell incubator environment. Polymers for the substrate 34 are an attractive material because they are largely biocompatible, and retain the optical clarity requirements while maintaining the ability to be easily defined through subtractive and additive micromachining. There are some attractive functional properties of the polymer used as polycarbonate in this example. These beneficial properties include resistance to cracking and well-known biocompatibility with respect to a host of cell lines.

Further details of various techniques of fabrication can be found in U.S. patent application Ser. No. 17/348,866, published as U.S. Patent Publication No. 2021/0394434; and U.S. patent application Ser. No. 17/805,478 filed Jun. 6, 2022, the disclosures which are hereby incorporated by reference in their entirety.

Additionally, for this application, the practical understanding of the potential for thermal loss was important. Internal calibration tests were performed and used prior to functional 3D MEA device 30 testing, which also served to test the supplemental thermal confirmation tools for use in validating the impedimetric readings.

Figure 3A:
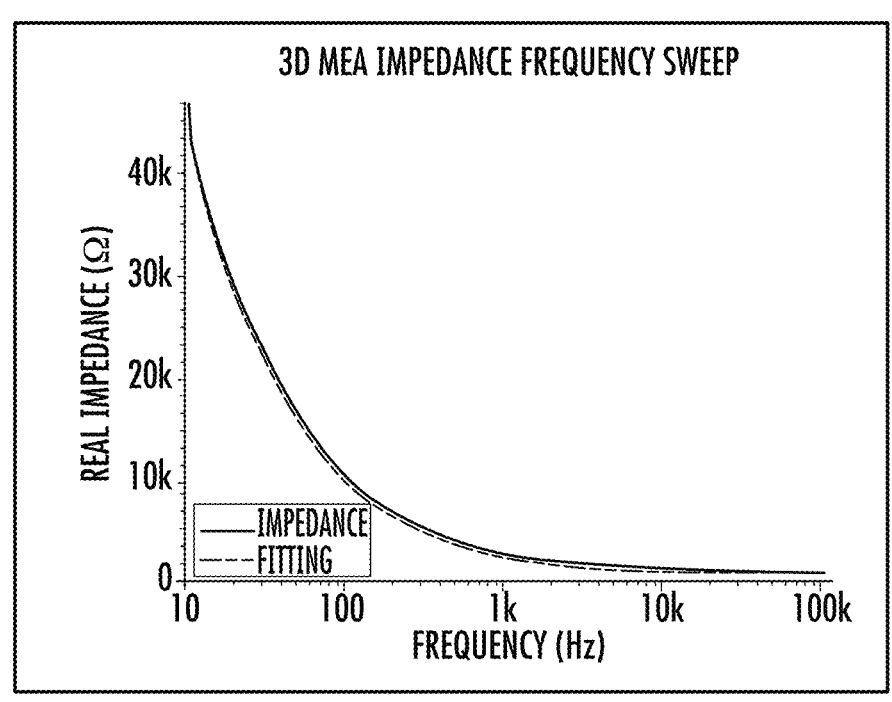
FIGS. 3A and 3B are graphs showing electrical impedance characterization of the 3D microelectrode array full spectrum impedance and phase measurements of the 3D microelectrode array device where the 1 kHz impedance of 2.76 kΩ, and a phase signature of −55° are well within literature defined values and the phase signature implying a more capacitive dominance of the circuit at 1 kHz, and showing how the Nyquist plot for this data helps determine other properties of the 3D microelectrode and the circuit inset of FIG. 3B, containing the equivalent circuit used in fitting the data.
Figure 3B:
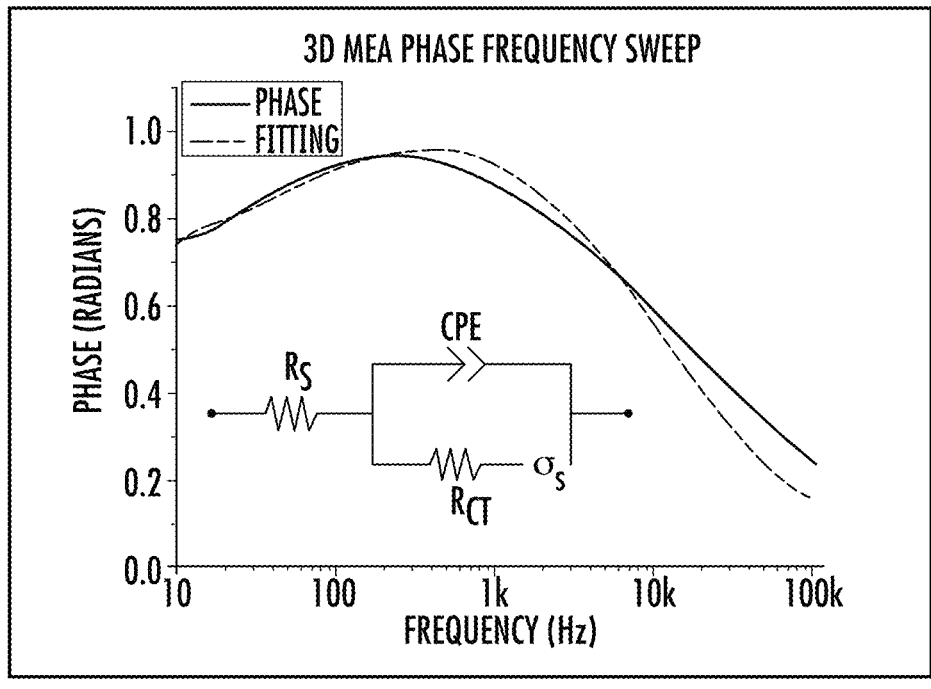
Figures 3C, 3D:
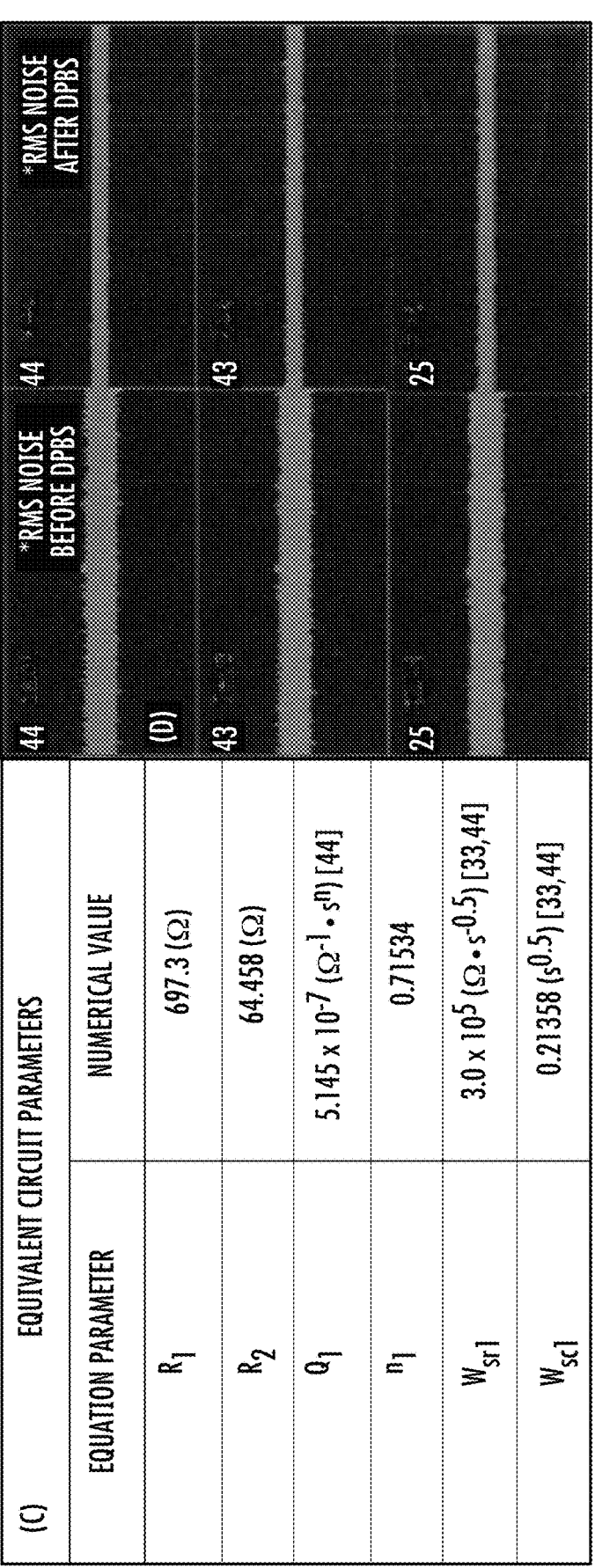
FIG. 3C is a table showing the resulting parameters for an equivalent circuit as a slightly modified Randles circuit with the switch to a CPE instead of a traditional capacitor.
FIG. 3D are graphs of sample channels from an Axion MUSE® electrophysiology recording system, showing RMS noise profiles of the 3D microelectrode array where the overall averaged RMS noise was reduced from 18.26 µV to 7.8 µV upon addition of electrolytes, suitable for electrophysiology.

FIGS. 3A-3D show graphs and a chart for the full spectrum impedance and phase results for the 3D MEAs (N=4). The 1 kHz impedance of 2.76 kΩ), and a phase signature of −55° are well within literature defined values. Using a custom Randles circuit, the 3D MEA device 30 was fitted to extract relevant circuit parameters, such as the Solution Resistance (RS), Charge Transfer Resistance (RCT), Double Layer Capacitance (CDL), and the Warburg Element (σ) (FIGS. 3A-3C). The accuracy of the fitting process was enhanced by incorporating a Constant Phase Element (CPE) in place of the standard CDL element.

Equation 1 defines the CPE, while Equations 2 and 3 list the Warburg-open (σo) and Warburg-short elements (σs) respectively, as defined by the EIS Analyzer software. Equation 4 contains the algebraic representation for the equivalent circuit used in fitting the 3D MEA device 30 and the extracted parameters are listed in the table of FIG. 3C.

Impedance of CPE:

$$Z(\omega) = Q^{-1}(\omega)^{-n} \tag{1}$$

Impedance of $\sigma_o$ and $\sigma_s$:

$$Z_{W_o}(\omega) = \frac{W_{or}}{\sqrt{\omega}}(1 - j)\coth\left[W_{oc}\sqrt{j\omega}\right], \tag{2}$$

$$Z_{W_s}(\omega) = \frac{W_{sr}}{\sqrt{\omega}}(1 - j)\tanh\left[W_{sc}\sqrt{j\omega}\right], \tag{3}$$

where:

$W_{or}$ or $W_{sr}$ = Warburg Coefficient, $W_{oc}$ or $W_{sc} = \dfrac{d}{D^{0.5}}$, $d$ = Nernst Diffusion Layer Thickness, $D$ = Diffusion Coefficient.

Impedance of 3D MEA:

$$Z_{MEA} = \frac{R_S(Z_1 + Z_{CPE}) + [(Z_1)Z_{CPE}]}{Z_1 + Z_{CPE}} \tag{4}$$

where:

$Z_1 = R_{CT} + Z_{\sigma_s}$.

The values and fitted signature imply a more capacitive dominance of the circuit at 1 kHz, which was experimentally hypothesized due to the usage of silver epoxy with enhanced surface porosity in the nanoscale to define the packaging traces 44. While various circuit elements may change the impedance and phase signatures of the 3D MEA device 30, it has not been fully established if these differential values across device fabrication approaches are large enough to impact the overall performance of the 3D microelectrodes 50 and 3D MEA device 30 itself.

For assessing the feasibility of using the uninsulated, 100 μm 3D microelectrodes 50 for cellular sensing, RMS noise measurements were obtained that helps provide a guide for performance. FIG. 3D is a representative screen capture image of a set of noise measurements of the 3D microelectrodes 50 and 3D MEA device 30 from before (left) and after (right) the addition of DPBS. In these examples, switching from air to DPBS as the conducting medium may result in a lower noise profile. Based on literature reported values that less than 10 μV is ideal for RMS noise values, compound cellular activity may be recorded. The example MEA devices 30 measured an average RMS noise value of ~7.8 μV after addition of DPBS, and illustrates the 3D MEA's suitability for obtaining electrophysiological recordings and potentially for stimulations.

For the temperature IDE 52a sensing modality, the frequency range to be used where temperature sensitivity was higher was determined. Since full spectrum impedance sweeps were performed, the analysis of different slices of spectra was performed to determine the ideal region for temperature sensing.

In a simple Randles circuit, the RS, RCT, and CDL values govern the Faradaic, kinetic electrochemical interactions present at higher frequencies, but also play a role along with the Warburg diffusion elements at the lower frequencies. In general, lower frequencies are susceptible to higher levels of environmental noise, which can produce unreliable results. Because the evaluation of temperature using an impedimetric sensor would be largely influenced by the energetic activation of dissolved ionic species in media, it was determined that higher frequencies were more likely to present a reproducible and consistent temperature change measurement.

Figure 4A:
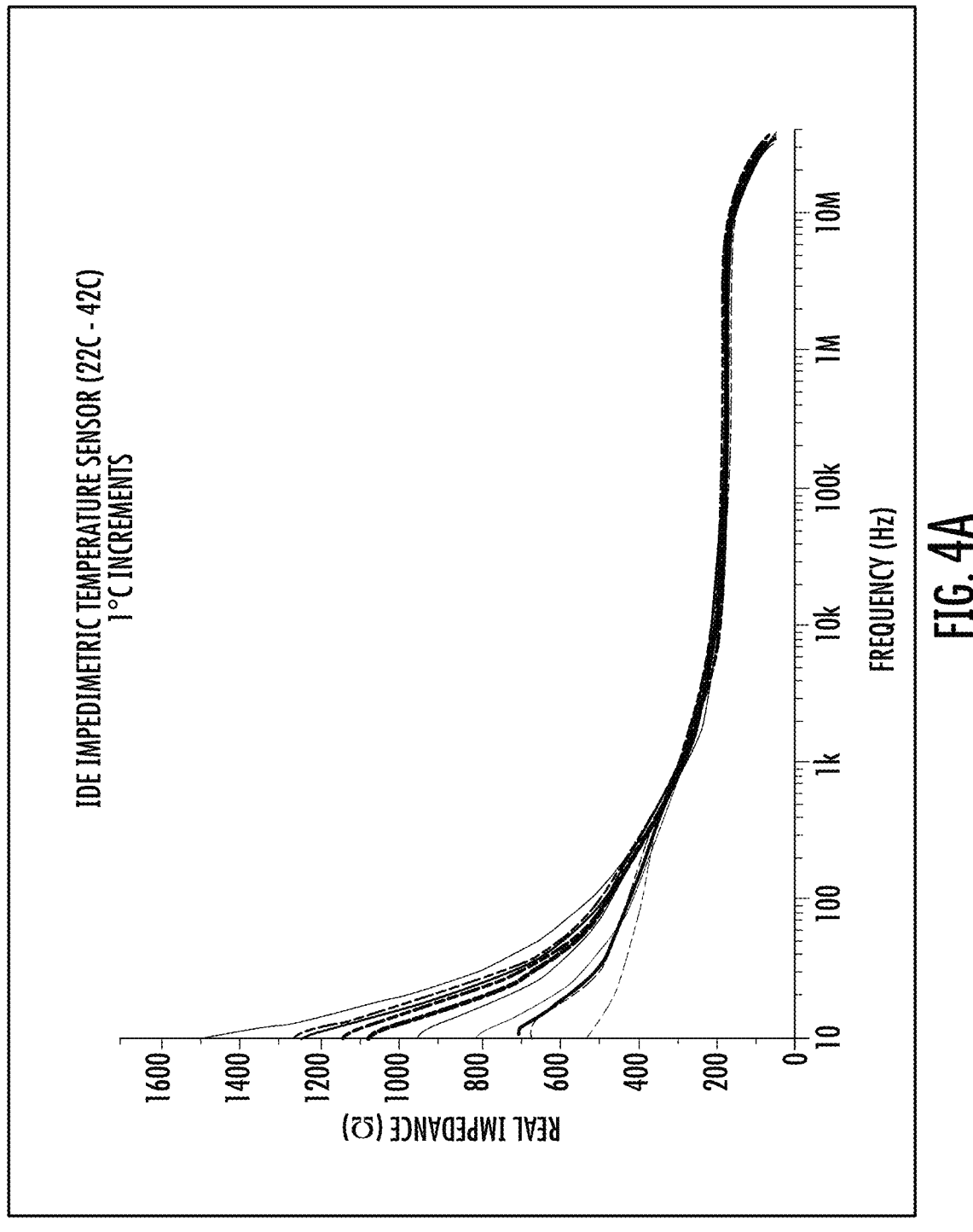
FIGS. 4A-4D are graphs showing electrochemical impedimetric characterization of the temperature sensing IDE using the attached microheater to varying DPBS temperatures, where

As the temperatures being measured were in the physiologically relevant range (22° C. to 42° C.) and were not high enough for a large amount of evaporation to occur, a decrease in impedance was expected due to increased ionic species motility. If temperatures of interest were much higher, then an increase in impedance would be expected with resultant relative increased concentrations of ionic species, from reduced solvent volumes. The results shown in the graph of FIG. 4A and indicates an overall expected trend of decreasing impedances as the temperature was increased.

Figure 4B:
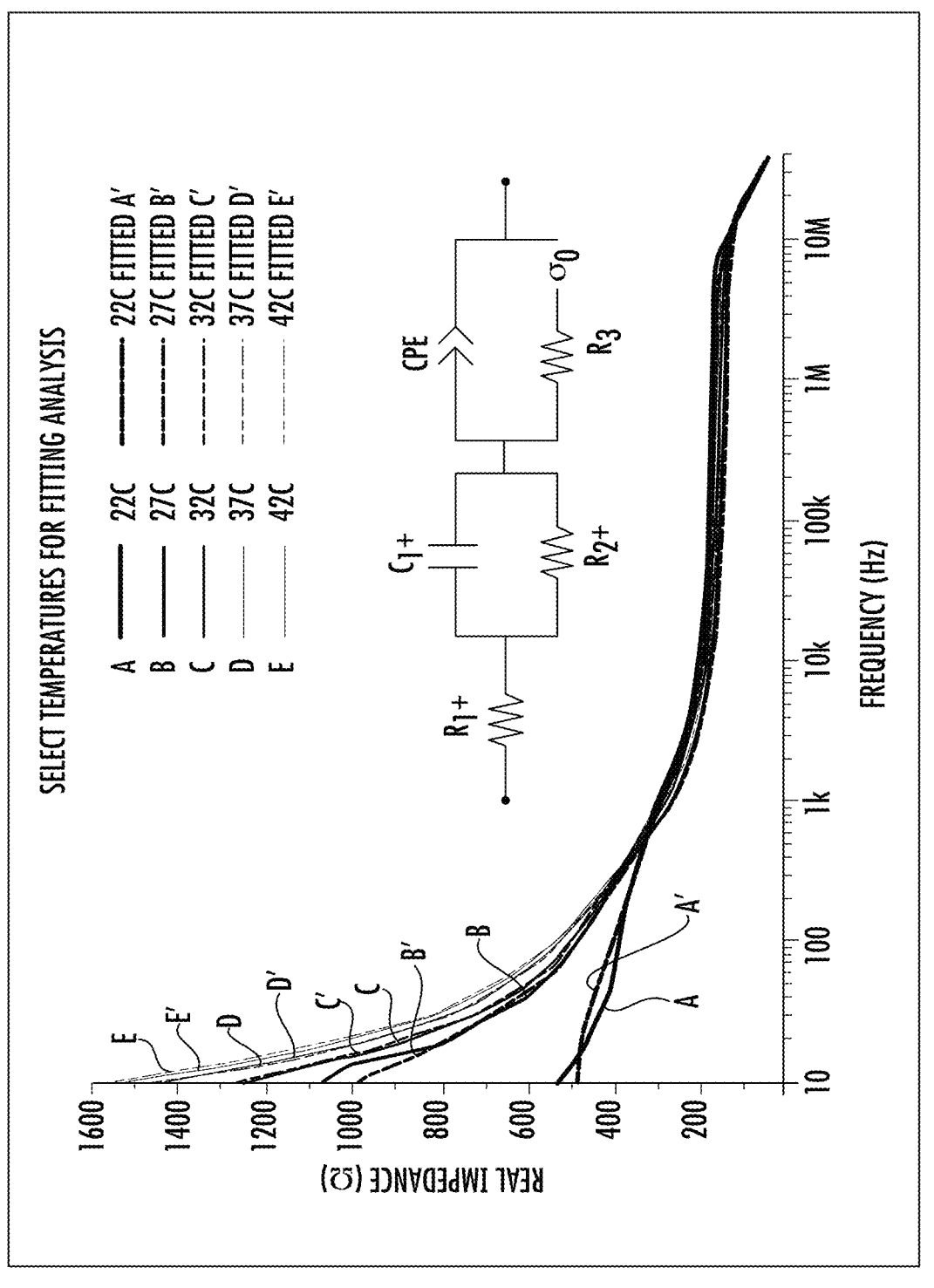
Figure 4C:
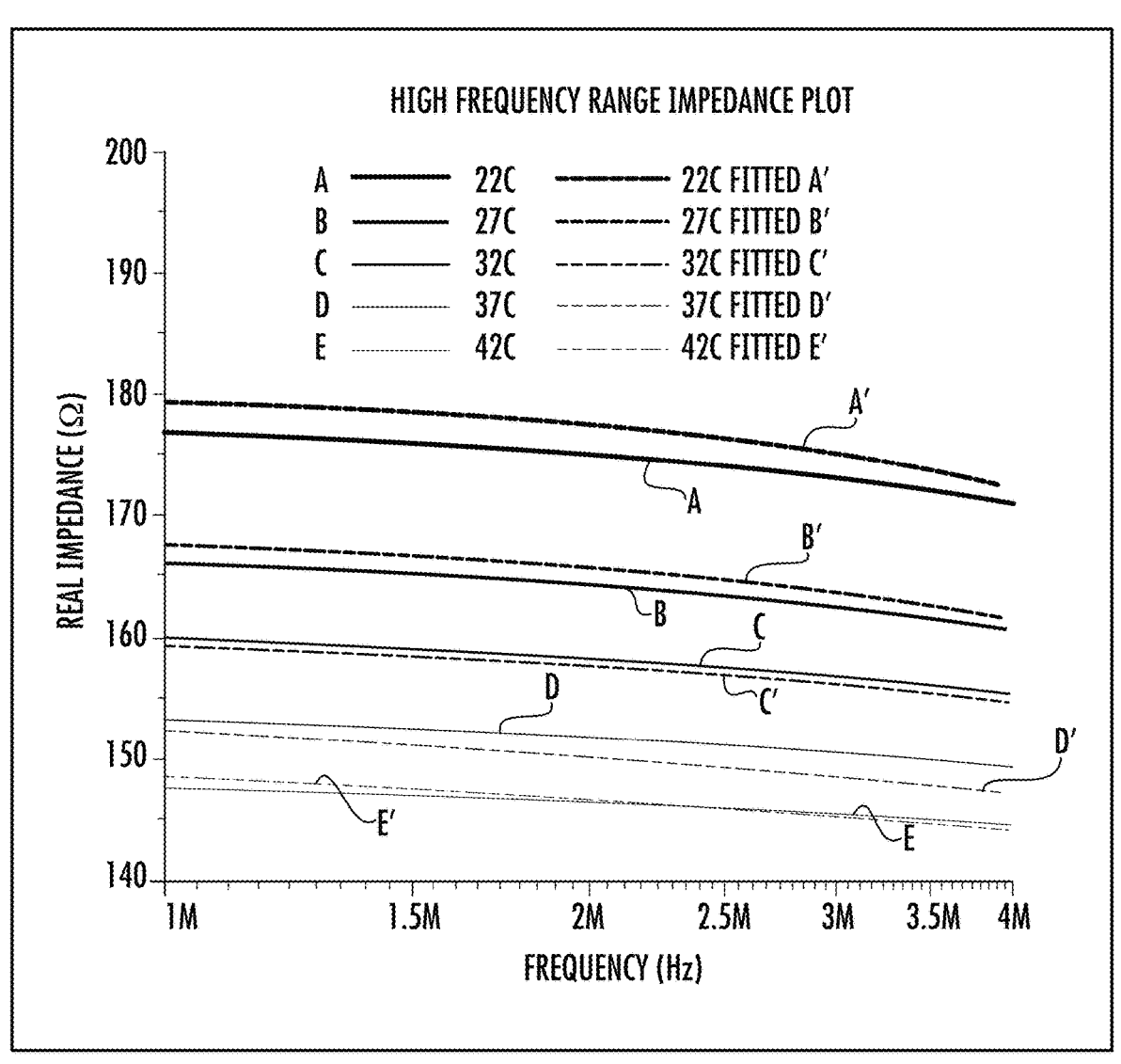
Figure 4D:
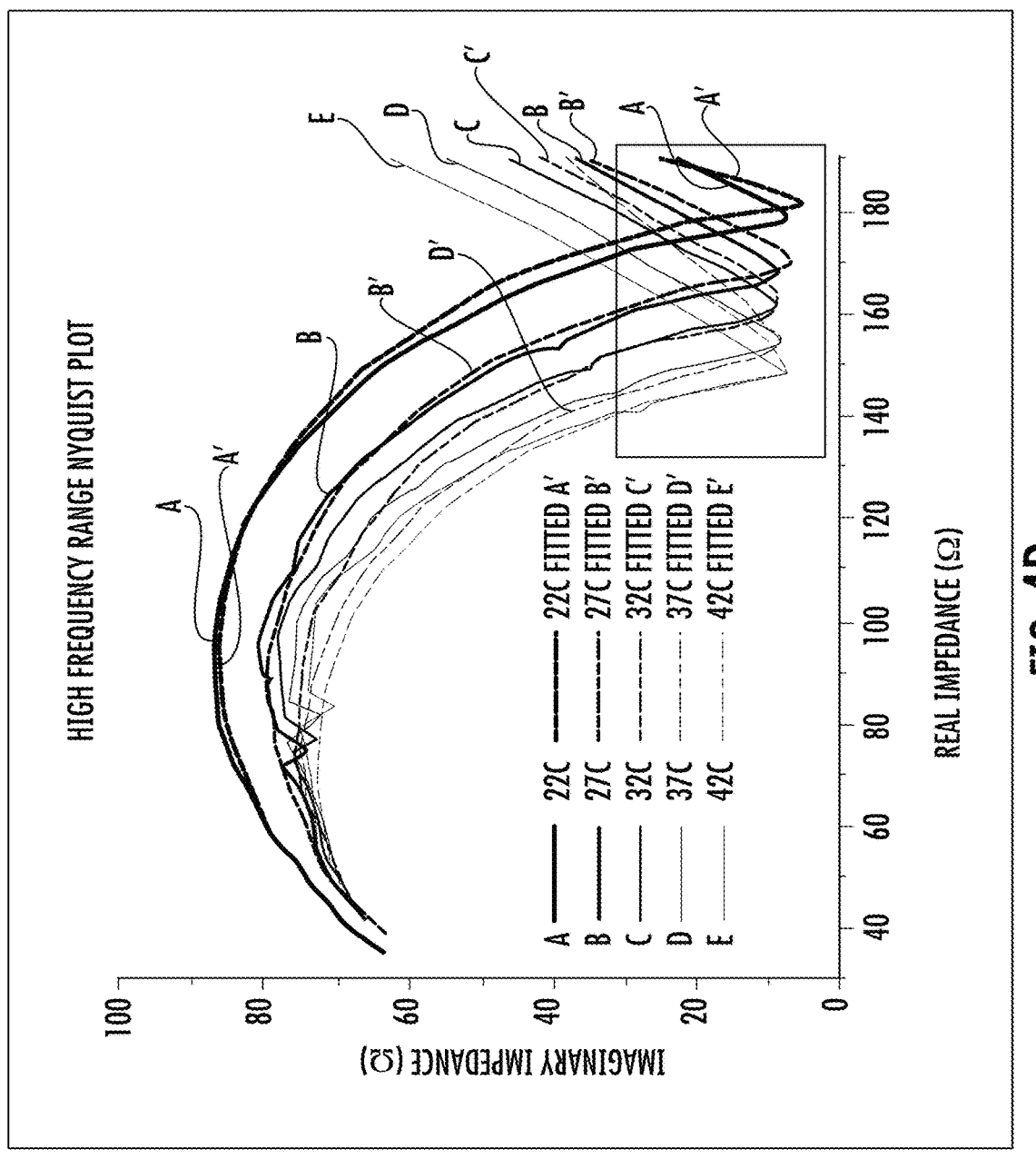

Similar to the 3D MEA device 30 fitting described above, a custom equivalent circuit was used to fit the temperature IDE 52a sensor. The circuit diagram for this custom equivalent circuit shown in FIG. 4B, along with the Impedance and Nyquist plots necessary to fully analyze this sensor configuration as shown in the graphs of FIGS. 4C-4D. The Nyquist plot becomes especially important for this IDE sensor as it illustrates how a traditional Randles circuit must be modified with additional circuit elements to account for secondary Faradaic regions that exist. It should be noted, however, that because the equivalent circuit is affected by a combination of circuit elements, especially with respect to the faradaic reactions, the RS is not the only element of consequence as in traditional impedimetric analysis, and thus, must be taken into account with both RCT, and CDL to fully characterize impedance changes observed at these higher frequencies.

Figure 4E:
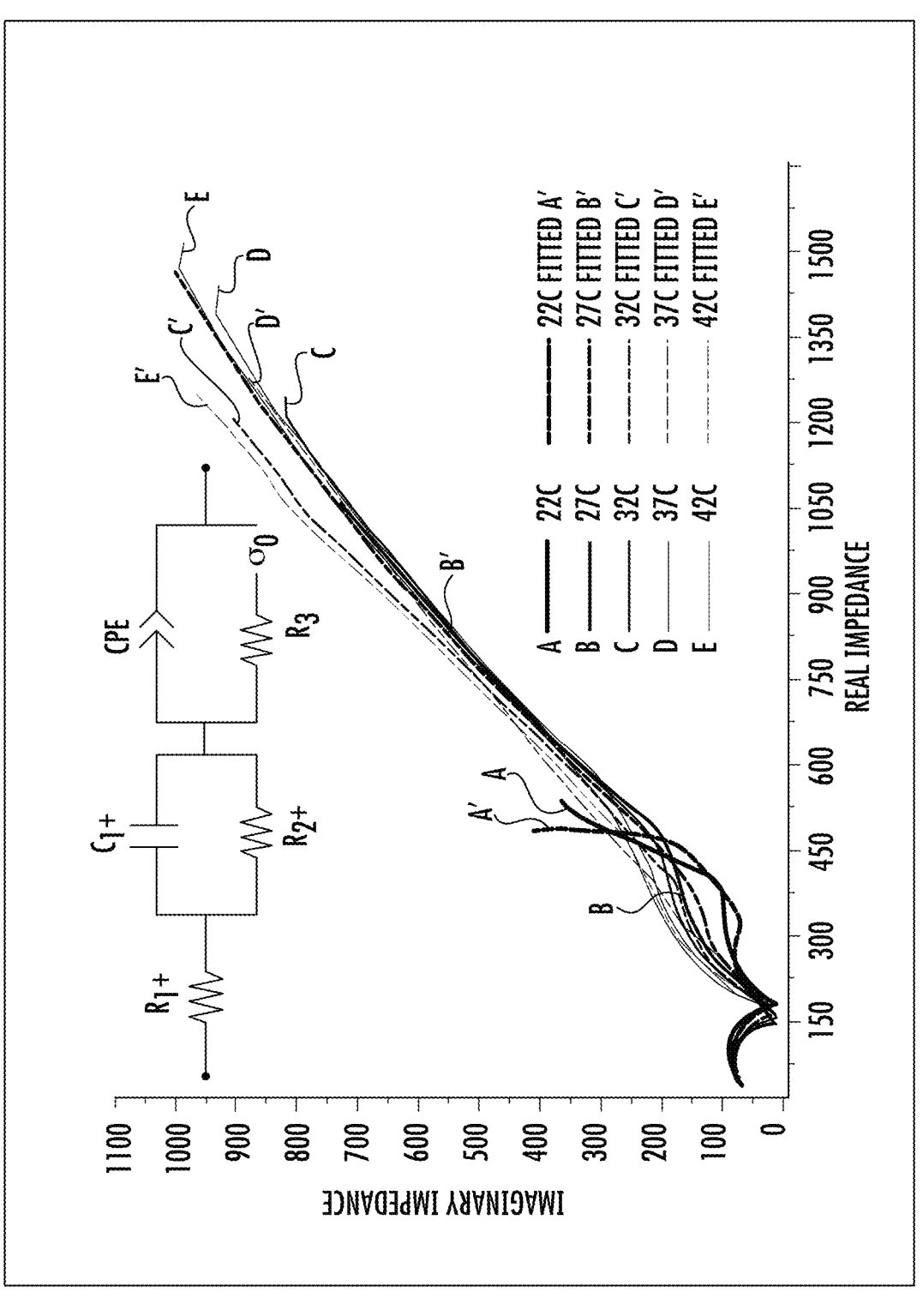
FIGS. 4E and 4F are additional graphs for the temperature sensing interdigitated electrode (IDE), where
Figure 4F:
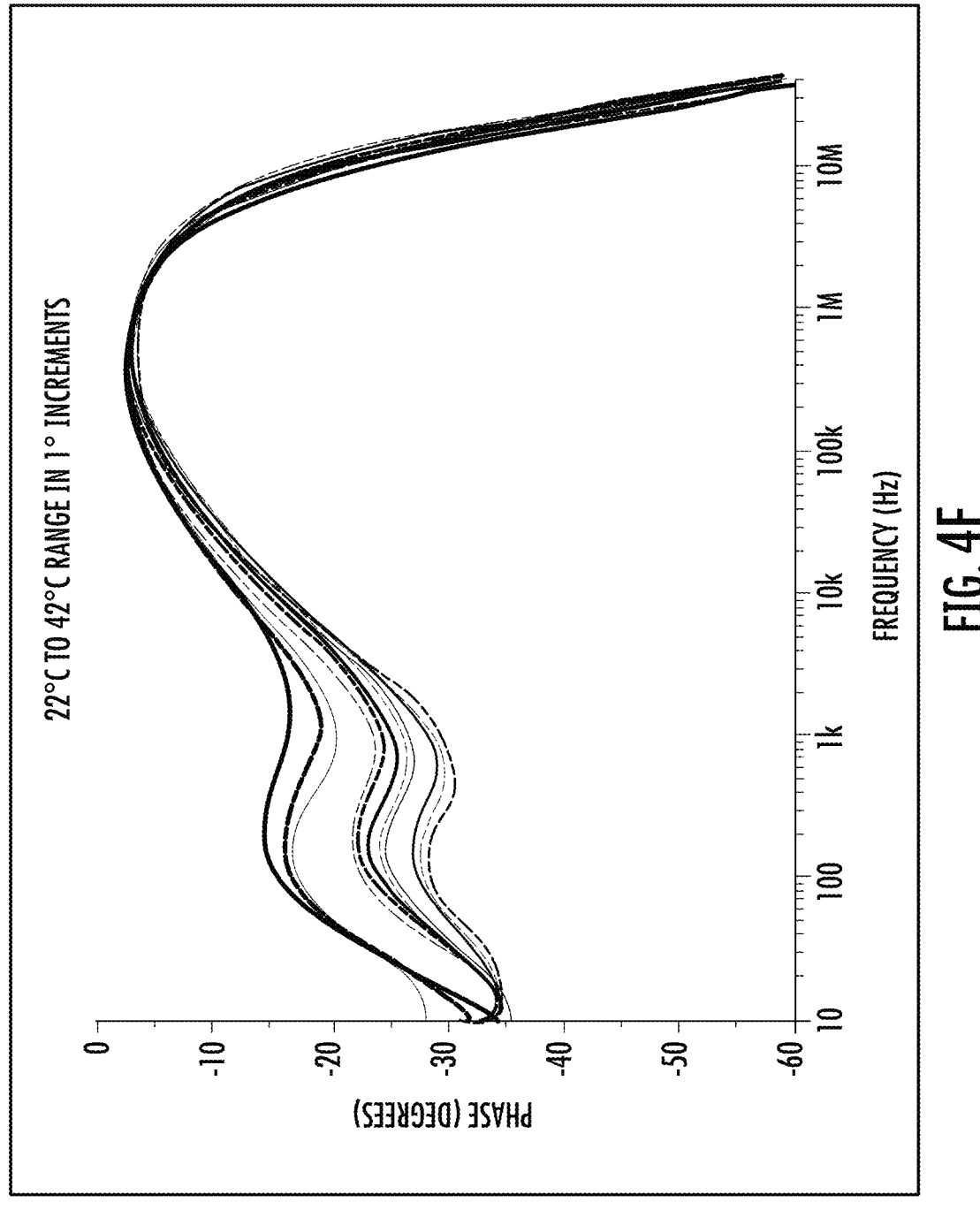

Equation 5 is thus justifiably different than Equation 4, as it accounts for new capacitive and resistive elements resulting from the differing circuit composition and materials. The values extracted from this fitting effort are shown in FIGS. 4E and 4F and the table in FIG. 4G. The calculation for the impedance of Go may be found in Equation 2.

Impedance of temperature-sensing IDE:

$$Z_{Tempurature} = \frac{R_{1*}(R_{2*} + Z_c*)(Z_1 + Z_{CPE}) + [(R_{2*}Z_{c*})(Z_1 + Z_{CPE})] + [(Z_1 Z_{CPE})(R_{2*} + Z_{c*})]}{(R_{2*} + Z_{c*})(Z_1 + Z_{CPE})} \qquad (5)$$

where:

$$Z_1 = R_3 + Z_{\sigma_o}.$$

Based on the frequency spectra evaluation, 1 MHz-10 MHz was generally determined to be the region of interest for temperature sensing where the data sets of N=4 were established. By using linear regressions, the adjusted regression value (R-square) of 0.97506 validated the observed consistent impedance trend decreasing across all tested temperatures. Incorporating the fitting model allowed for the frequency band of interest to be narrowed to 1 MHz to 4 MHz by using a sample subset of temperatures spanning the tested range (FIGS. 4B-4C). This selection was again confirmed using the experimental and fitted Nyquist plots, which demonstrated a measurable leftward-shift of the first Faradaic curve, corresponding to these higher frequency regions of interest. Specifically, this is in reference to the inverted peak highlighted in FIG. 4D which is primarily governed by R1*and R2*, which is denoted because this equivalent circuit is not a true "Randles" circuit, and thus, they are not necessarily directly equivalent to RS and RCT.

To confirm the inability to use the lower frequencies for temperature sensor measurements, linear regressions were also calculated from 10 Hz to 100 Hz (not shown). The observed R-square value of 0.65958 supported the hypothesis that potentially noise and general inconsistencies across readings in this region, would produce unreliable temperature sensor readings.

Fortunately, there were many options when developing an antibody conjugation protocol for a surface with Au as the functional layer. It has been well established that free Thiol groups permit adsorption to Au-metal surfaces, which provides an opportunity for simple antibody conjugation, though potentially in an admittedly non-directional specific manner. However, an evaporative metallization process, such as electron beam physical vapor deposition, produces a similar high surface area metal layer for more potential antibody binding. Many different antibodies may be used and attached via chemistries or via thiol-mediated adsorption to gold or other materials. Examples of antibodies may include antibodies for insulin, pyruvate, Vitamin D and others.

Plasma treatment was introduced to enhance the binding affinity of the antibodies to the Au surface, although in subverting conjugation chemistries, some minimal loss of antibodies was expected. Anti-L-Glutamine antibodies were selected for characterizing this analyte sensor, as L-Glutamine is a critical component in cell culture media. As an example, it may find use as a potential screening target during assays, because although it is a necessary component, it degrades readily into toxic ammonia, which may be utilized an indirect indication for necessary media changes. As an alternate application, it shows potential for cancer studies.

Figure 5A:
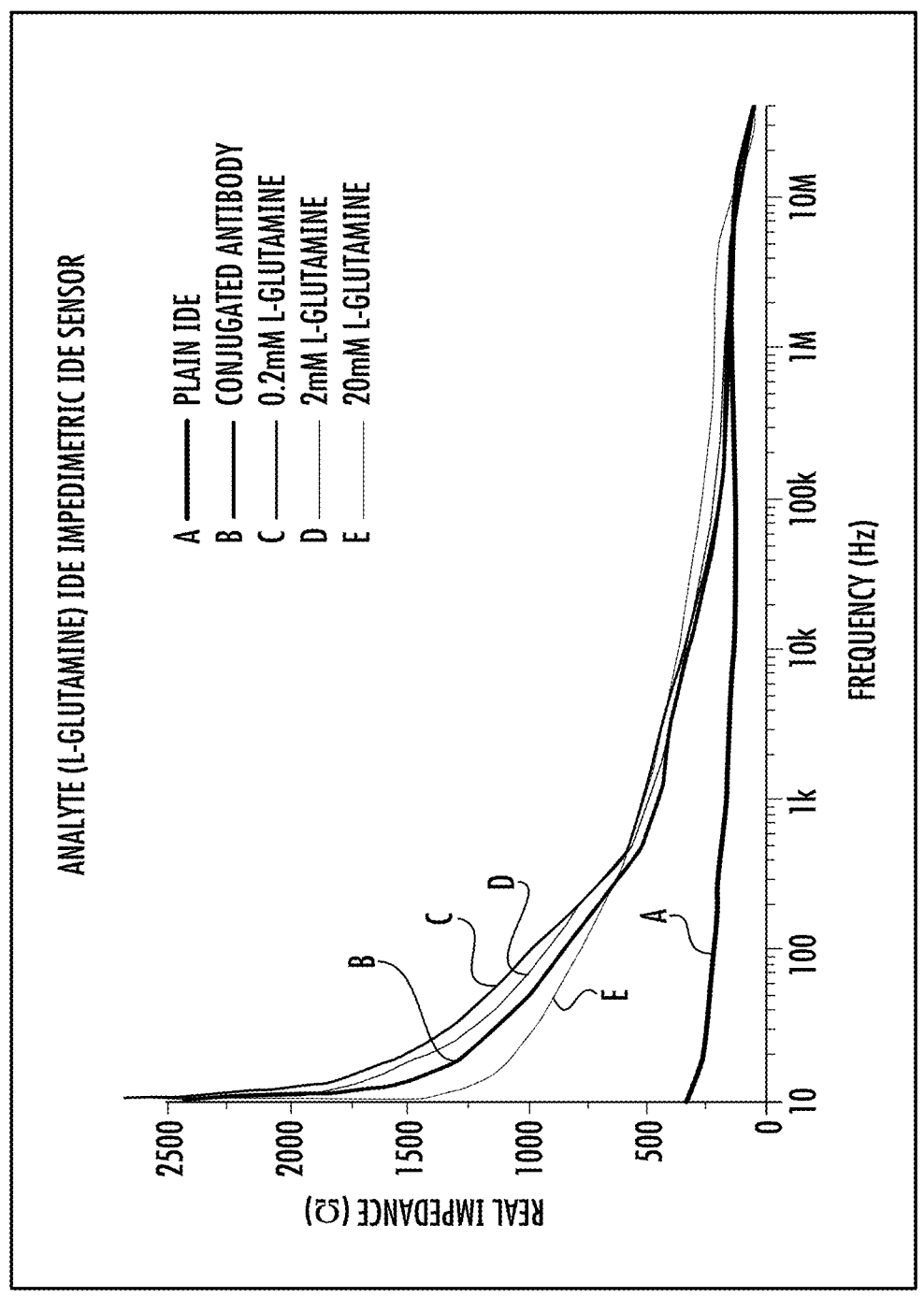
FIGS. 5A-5G show electrochemical impedimetric characterization of the analyte IDE as a sensor, where
Figure 5B:
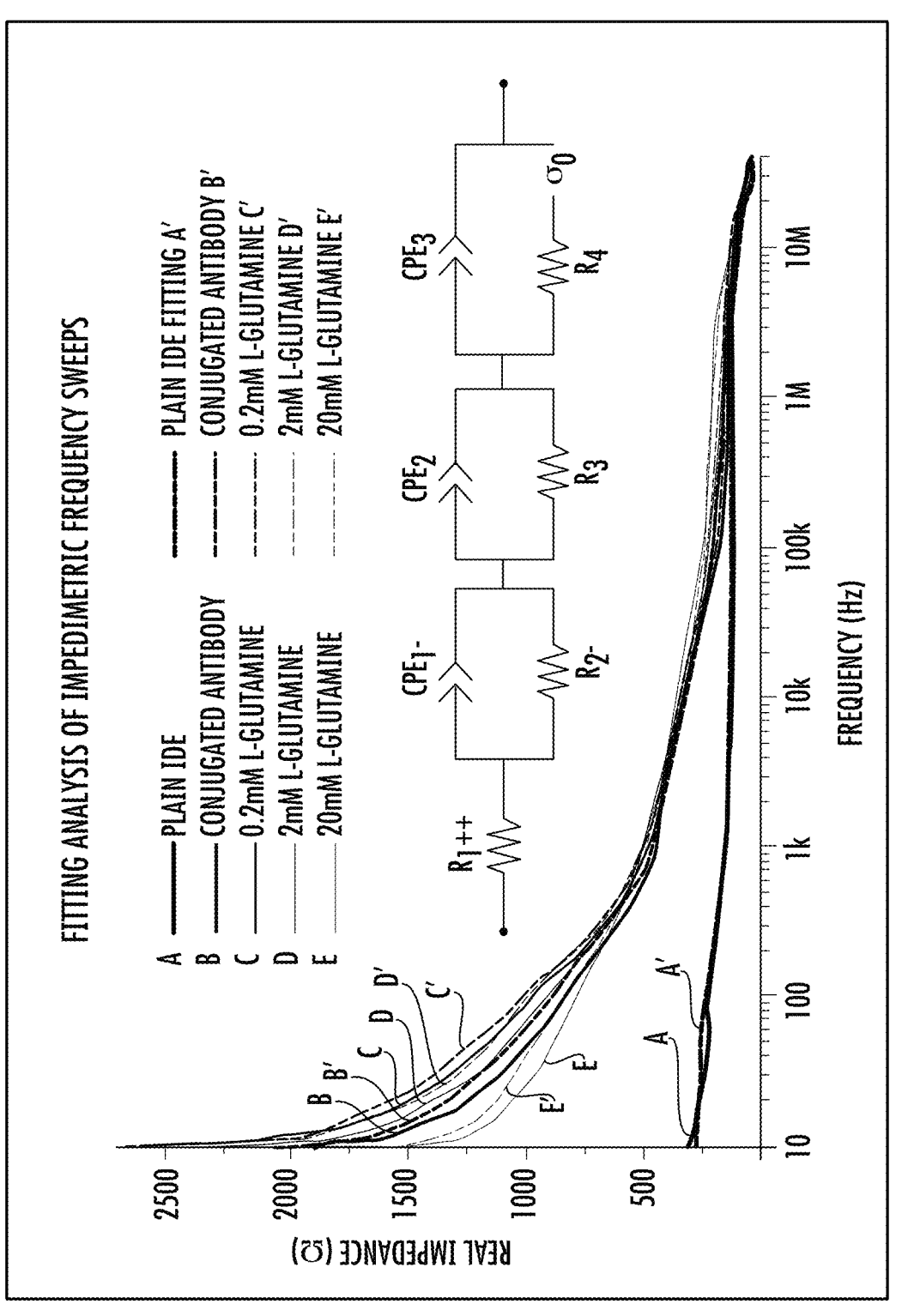
Figure 5C:
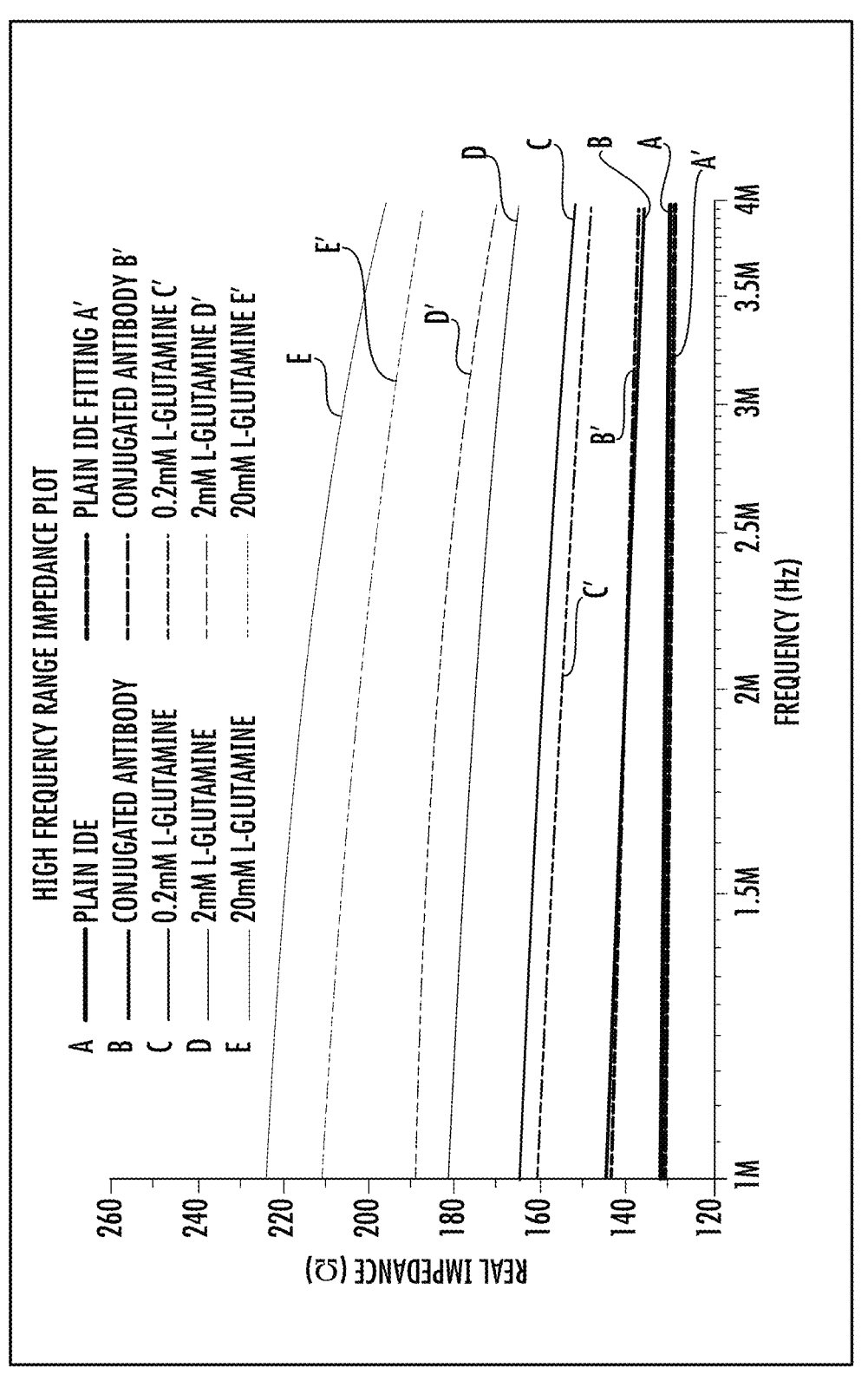
Figure 5D:
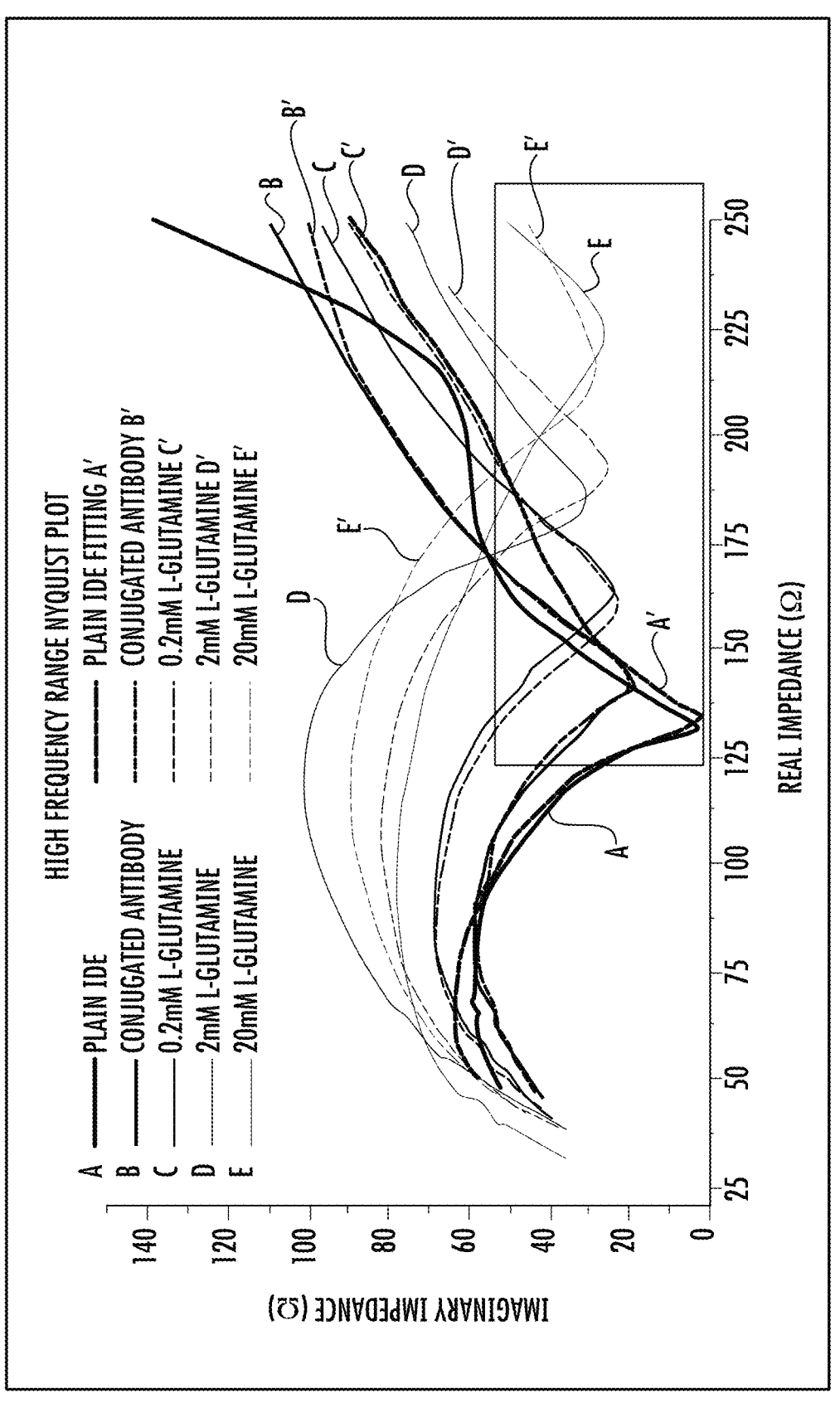

Full spectrum impedance sweeps were performed for the analyte sensing IDE 52*b* (FIG. 5A). Similar to the temperature IDE 52*a*, the expected frequency region of interest was located in the higher frequency range between 1 MHz-4 MHz, due to the functional changes expected through conjugation of the antibodies atop the IDE. A change in the capacitive component of the equivalent circuit was expected once the antibody was conjugated, and this was confirmed both through fitting (FIGS. 5B-5D) and in the phase plots shown in FIG. 5I. The extracted equivalent circuit parameters for analyte sensing IDE are shown in Table 2 with reference to FIGS. 5H and 5I.

In order to model the conjugating antibodies on the surface of the IDE 52*b*, another CPE element in parallel with R4 was added to the equivalent circuit to present additional dielectric layers in the signal pathway. This modified the resulting equation for the analyte-sensing IDE (Equation 6), which has been simplified as shown:

Impedance of analyte-sensing IDE:

$$Z_{Analyte} = \frac{R_{1}\alpha + (Z_{CPE_{1}R_{2**}}\gamma\delta) + (Z_{CPE_2}R_3\beta\delta) + (Z_{CPE_3}Z_1\beta\gamma)}{\alpha}, \quad (6)$$

where:

$$Z_1 = R_4 + e_{\sigma_o},$$
$$\alpha = \beta\gamma\delta,$$
$$\beta = R_{2} + Z_{CPE_{1}},$$
$$\gamma = R_3 + Z_{CPE_2},$$
$$\delta = Z_1 + Z_{CPE_3}.$$

Again, as this more complex equivalent circuit was not a traditional Randles model, the components relating to the first Faradaic curve of interest had been denoted with () in Equation 6. This was labeled to highlight their relative placement in the equivalent circuit in comparison to a more traditional set of RS, RCT, and CDL, and are thus R1, R2, and CPE1. The values for these fitted models may be found in the supplementary information shown in the table of FIG. 5J. Similarly, the calculation for the impedance of σo may be found in Equation 2. The unconjugated or plain IDE was fitted with the same equivalent circuit due to the IDE having the same fabricated structure.

Similar to the temperature sensor, a linear regression was used to calculate the R-square value for this sensor, and the resulting value of 0.90517 provided an affirmative indication of its effectiveness in sensing the differential concentrations of L-Glutamine across the 0.2 mM-20 mM range.

Examining solely the overall frequency plot of the impedance (FIG. 5A), it was evident that the 2 mM and 20 mM L-Glutamine concentrations appeared to have reached a saturation point of the sensor configuration. However again, previous impedimetric sensor studies have shown that the frequency range may be tuned to the analyte of interest, and the higher frequencies would provide relevant faradaic changes. Upon closer inspection of the 1 MHz-4 MHz region, a consistent pattern (N=4) was observed, and this is supported both by the Nyquist plot and the fitting of the experimental readings. A well-defined increase was impedance is observed at the end of the first Faradaic curve in the Nyquist curve governed by R1and R2.

The change in the curve shape, and the impact of the imaginary part of impedance, indicate that concentrations increase. This is likely due to an impact on the capacitive circuit elements governed by CPE1**, which are imposed by the addition of the antibodies and the L-Glutamine in solution. The probable saturation of the sensor could additionally be due to the robustness of the antibody adherence to the Au-surface, which successive wash steps could impact, along with the impacts of the total surface area of the IDEs that may not be optimized for this particular analyte reaction. By using a surface assembled monolayer (SAM) and conjugation chemistry, the orientation of the antibodies can be controlled along with the longevity of their adherence to the IDE. However, such a process may introduce potentially hazardous elements into a MPS, and increase the complexity of the microfabrication approach.

Figure 5E:
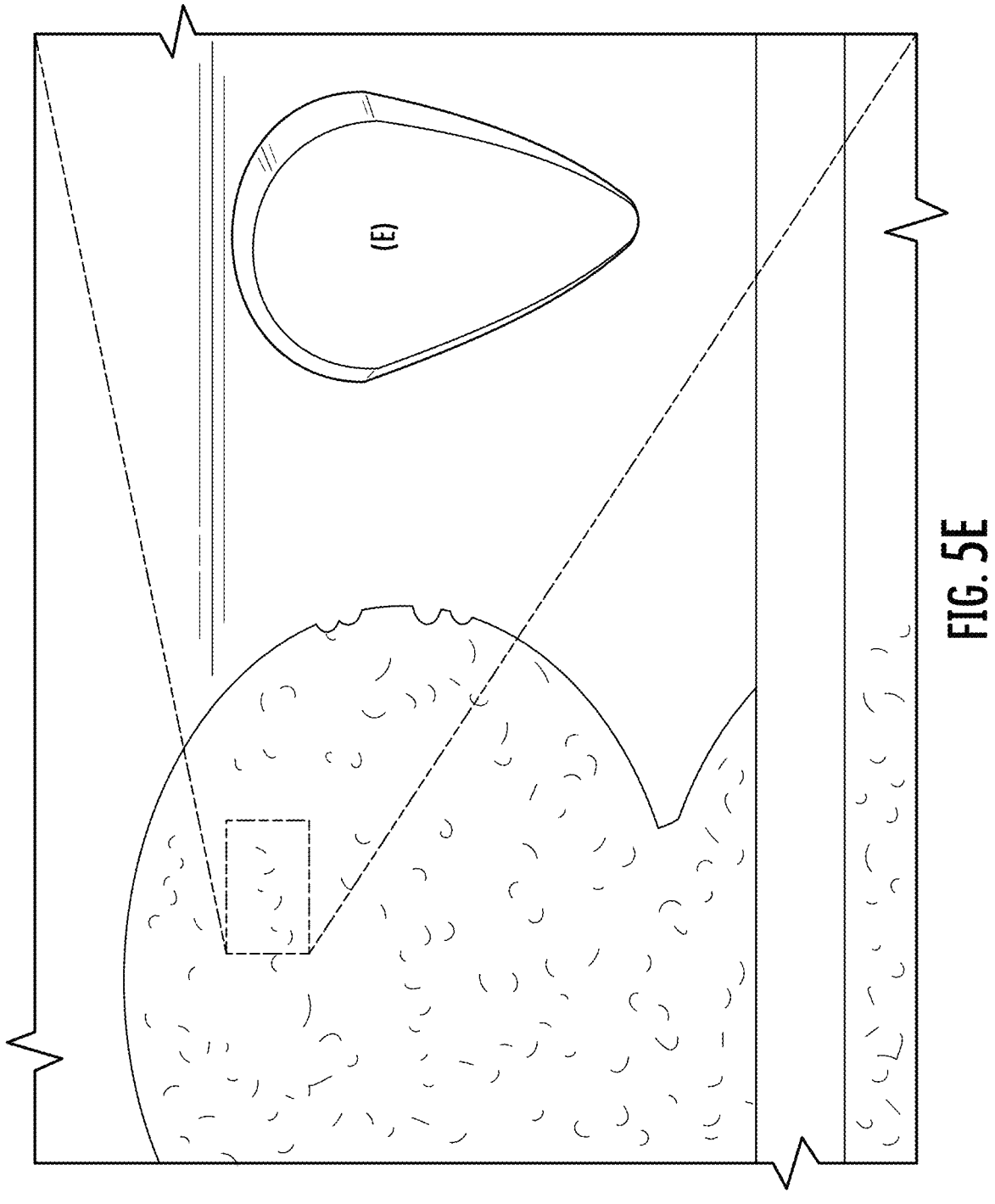
Figure 5F:
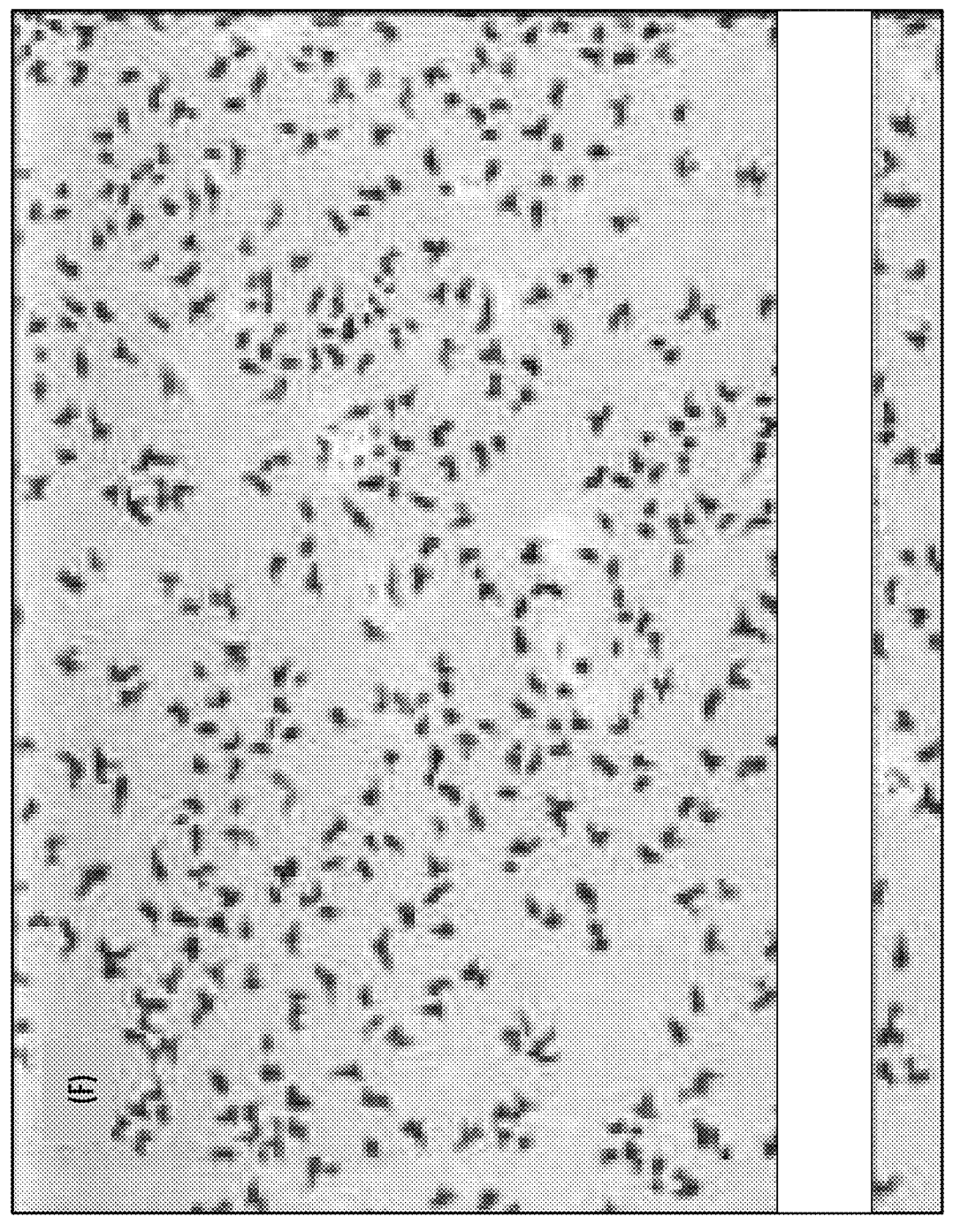
Figure 5G:
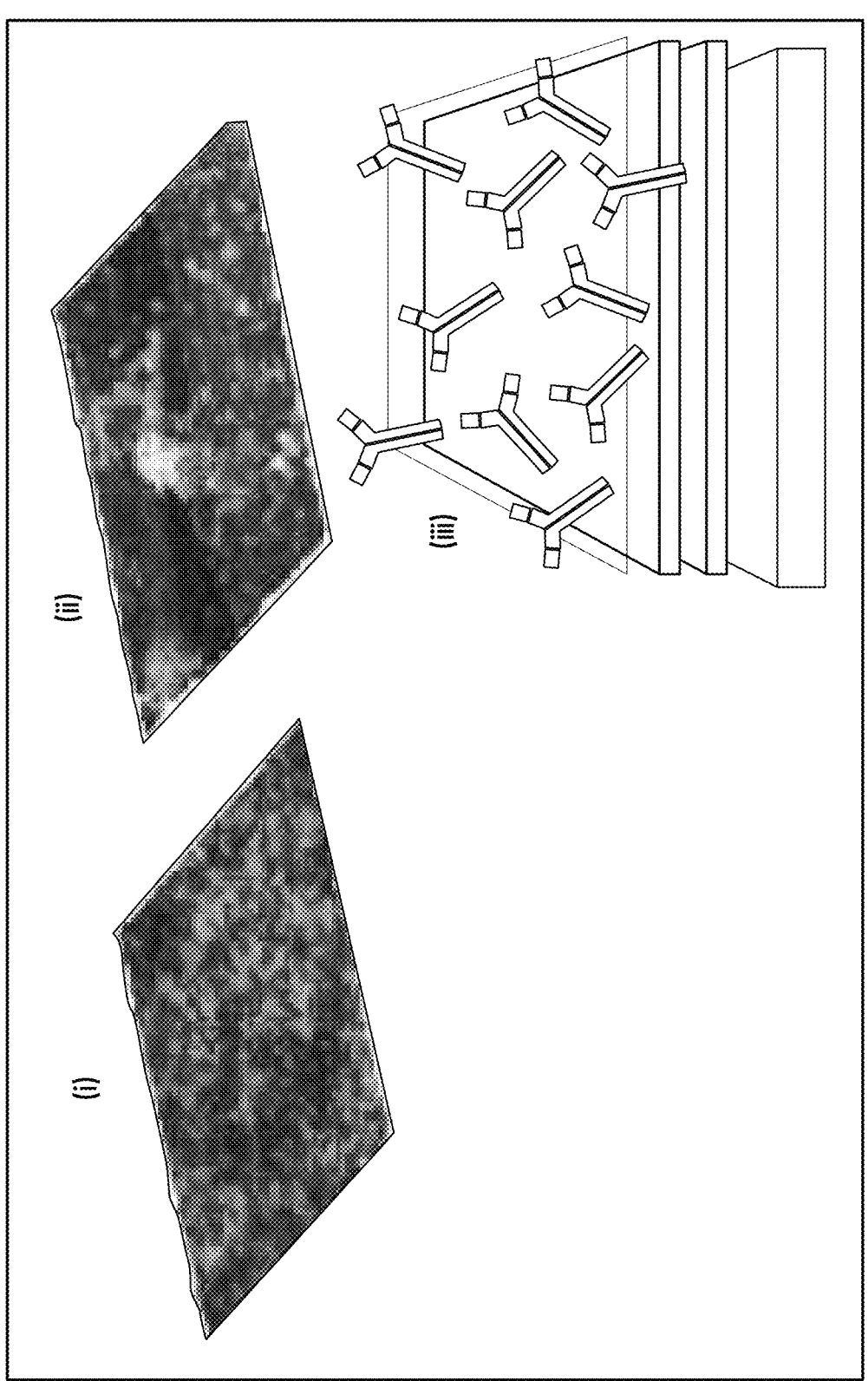
Figure 5H:
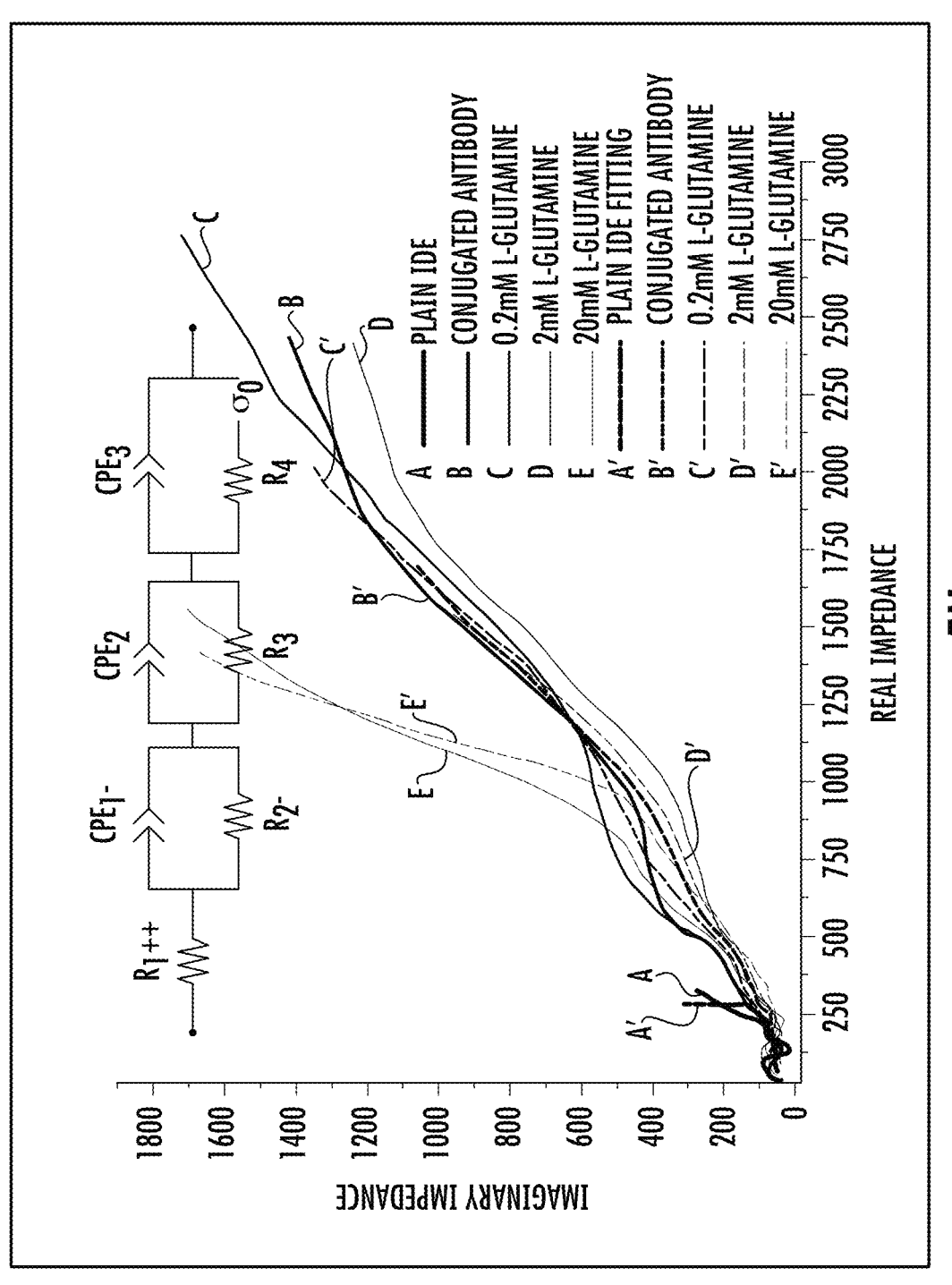
FIG. 5H is a graph for the analyte sensing IDE based on FIG. 5A showing the full Nyquist plot for the fitted and experimental results for the tested conditions and the inset for the reference, including the equivalent circuit of the conjugated sensor, and for the tested concentrations of L-Glutamine.
Figure 5I:
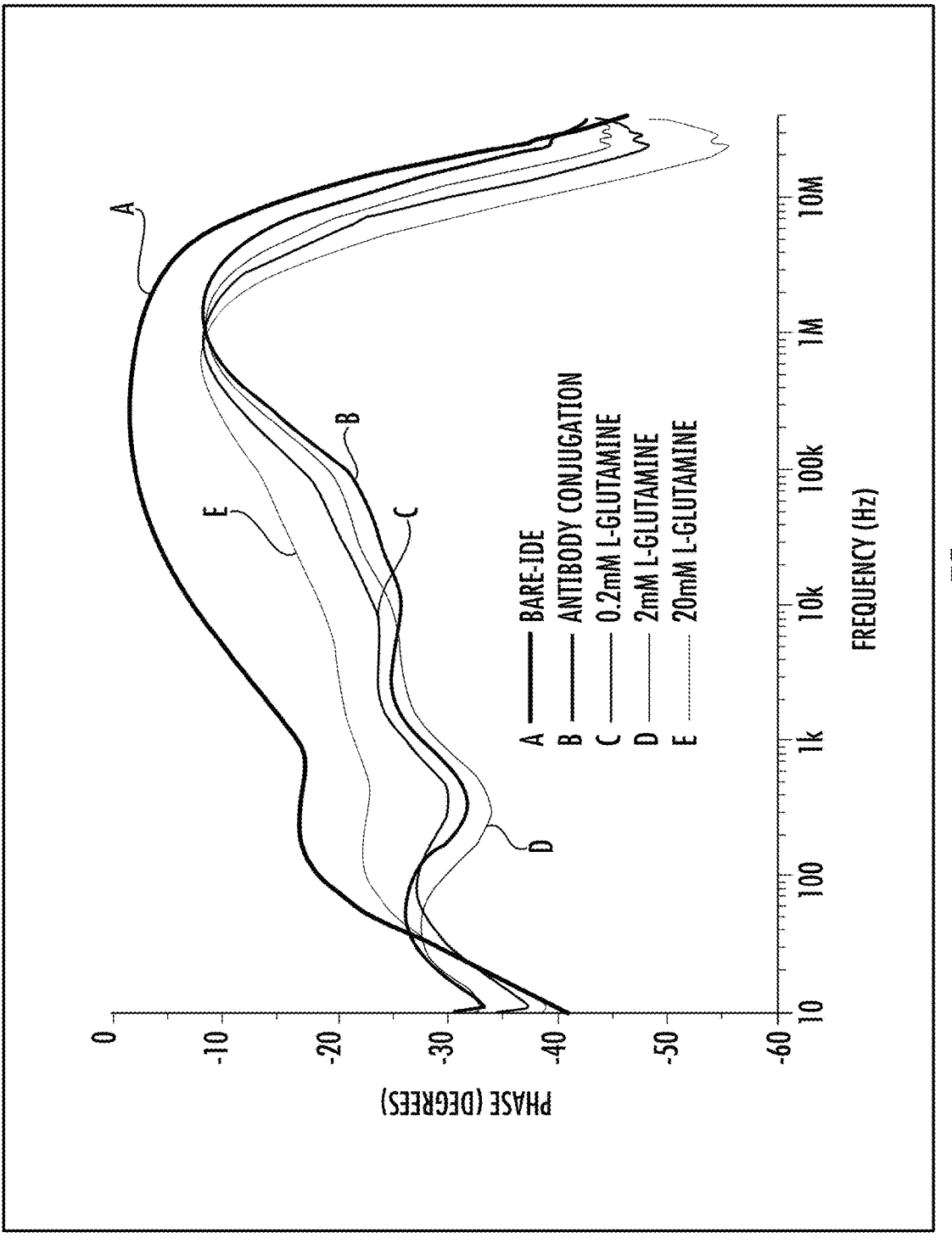
FIG. 5I is a graph of the full spectrum phase plot for the tested conditions.

FIG. 5E is an SEM image of the Ti-Au IDE configuration, along with a single 3D microelectrode of the assembled device. SEM images showcasing the plasma-conjugated antibodies on the Au IDE surface are shown in FIG. 5F. AFM images for the IDE are additionally shown in FIG. 5G. The unconjugated surface of the IDE 52*b* may be observed in FIG. 5G (i), which has a lower surface roughness (<12 nm) present from the evaporated metal. This is contrasted with FIG. 5G (ii) which contains the conjugated antibodies. Larger average roughness (<66 nm) can be observed in this image, including a fairly large grouping of the antibodies indicate by the arrow. These results show the functionalization of the IDE surface, and the layered fabrication of the analyte sensor is schematically represented for illustrative purposes in FIG. 5G (iii). It also illustrates how a simple plasma treatment regimen can be used to avoid complex conjugation chemistries. However, one disadvantage of this method is in the irregularity of drop casting the antibody solution without any conjugation chemistries. While simple and effective, for more sensitive applications, a SAM-mediated approach may be necessary to achieve optimized surfaces and reaction rates.

Figures 6A, 6B, 6C:
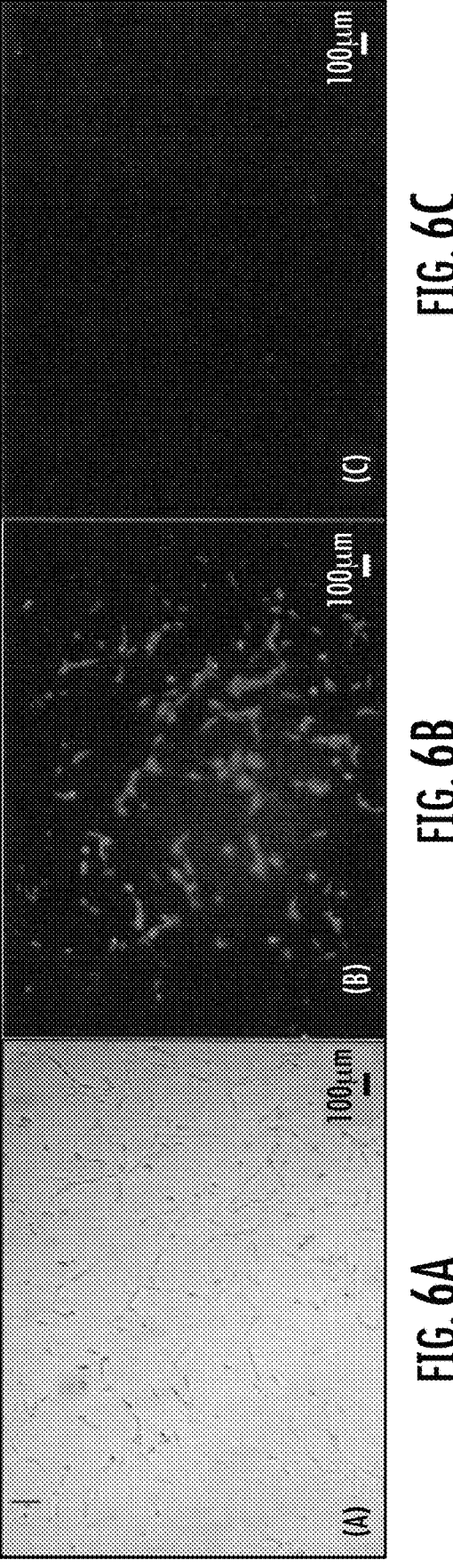
FIGS. 6A-6C show optical and fluorescent images of C2C12 myocyte cells on the device at 5 DIV, demonstrating the optical clarity of the fabricated device, as well as excellent cell viability, where

FIGS. 6A-6C include optical and fluorescent confocal microscopy images of a C2C12 culture grown on the 3D MEA device 30, in accordance with a non-limiting example, at 5 days in vitro (DIV). These images were obtained using transmitted light microscopy and illustrate the ability of these devices to retain optical clarity, even after the incorporation of each additional modality of sensing. This result also serves to illustrate that the polymer as the substrate 34 is suitable for transmission of both excitation wavelengths necessary to use Calcein AM and Propidium Iodide. Cellular morphology of C2C12 cells were comparable to other reported approaches and Calcein AM stain ratios illustrate that the biocompatibility of the chip overall was excellent (>97%).

Figure 6D:
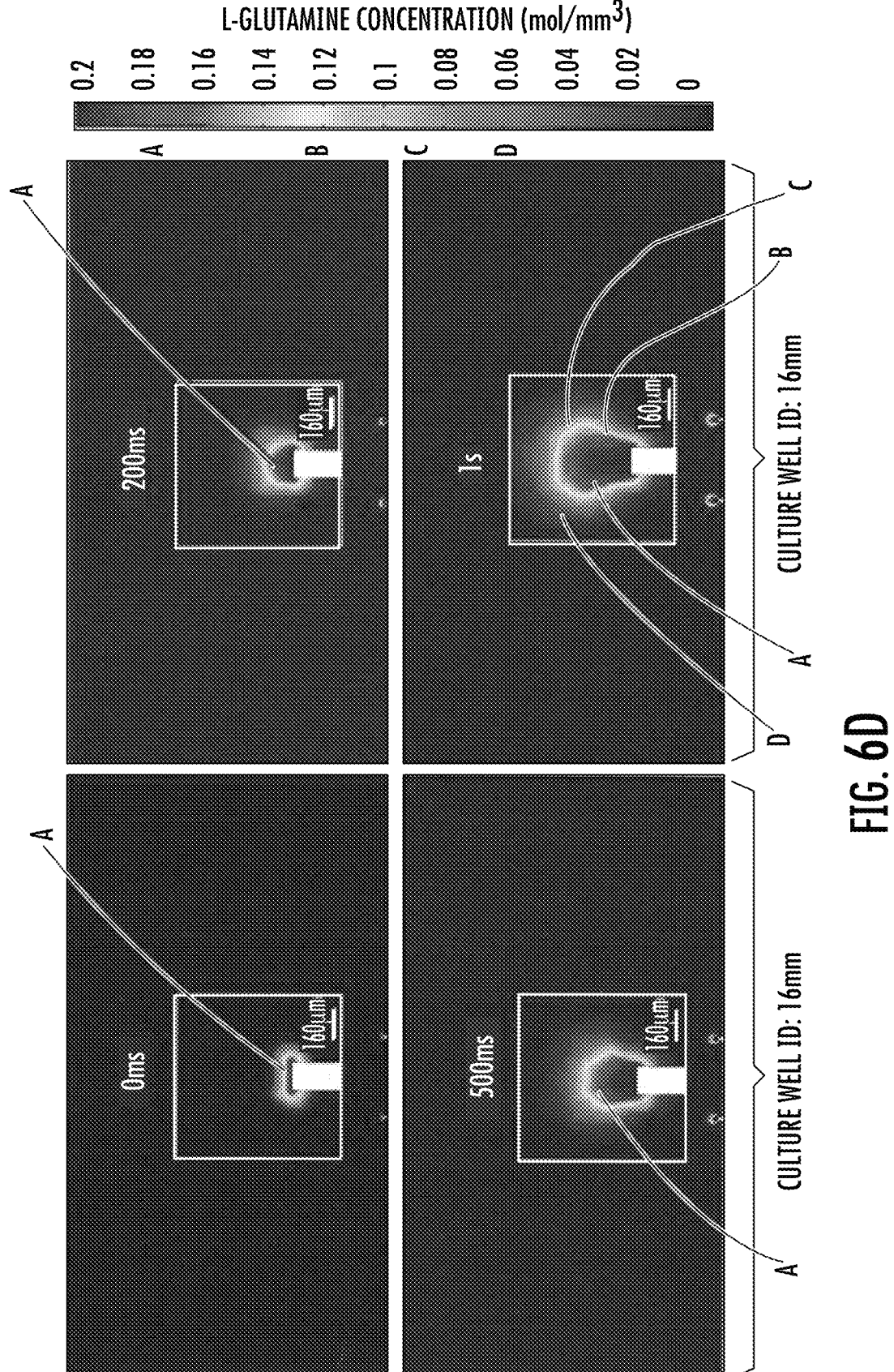
FIG. 6D shows COMSOL microfluidic modelling of the device with a constant 8 Pa applied pressure and showing the time points 0 ms, 200 ms, 500 ms, and 1 second post application where the time point is reflective of the localized application of the simulated L-Glutamine and the images are enlargements of a port at each time point to better visualize the concentration changes with scale bars for inset images only. At 0 s, there is no substantial ingress of the simulated 0.2 mM L-Glutamine solution. At 200 ms and also at 500 ms, the solution is still highly localized near the inlet. At 1 s, the solution is still localized, however, this time point is the maximal time where pressure should be applied to retain local chemical stimulation. Additional time points for the COMSOL fluidic model, with continuously applied 8 Pa pressure on the inlets.

The images shown in FIG. 6D illustrate the results of COMSOL fluidic modelling performed to assess the feasibility for localized application of compounds in a defined culture area. With a nominal 8 Pascal of force consistently applied over time, the 0.2 mM solution was locally concentrated under the 1 s time point as shown in the lower right-hand image. Across the span of time points shown (0 ms, 200 ms, 500 ms, 1s) the solution was controllably dispersed, which would allow for precise volumetric injection of say a spheroid located atop the port.

Figures 6E, 6F, 6G, 6H:
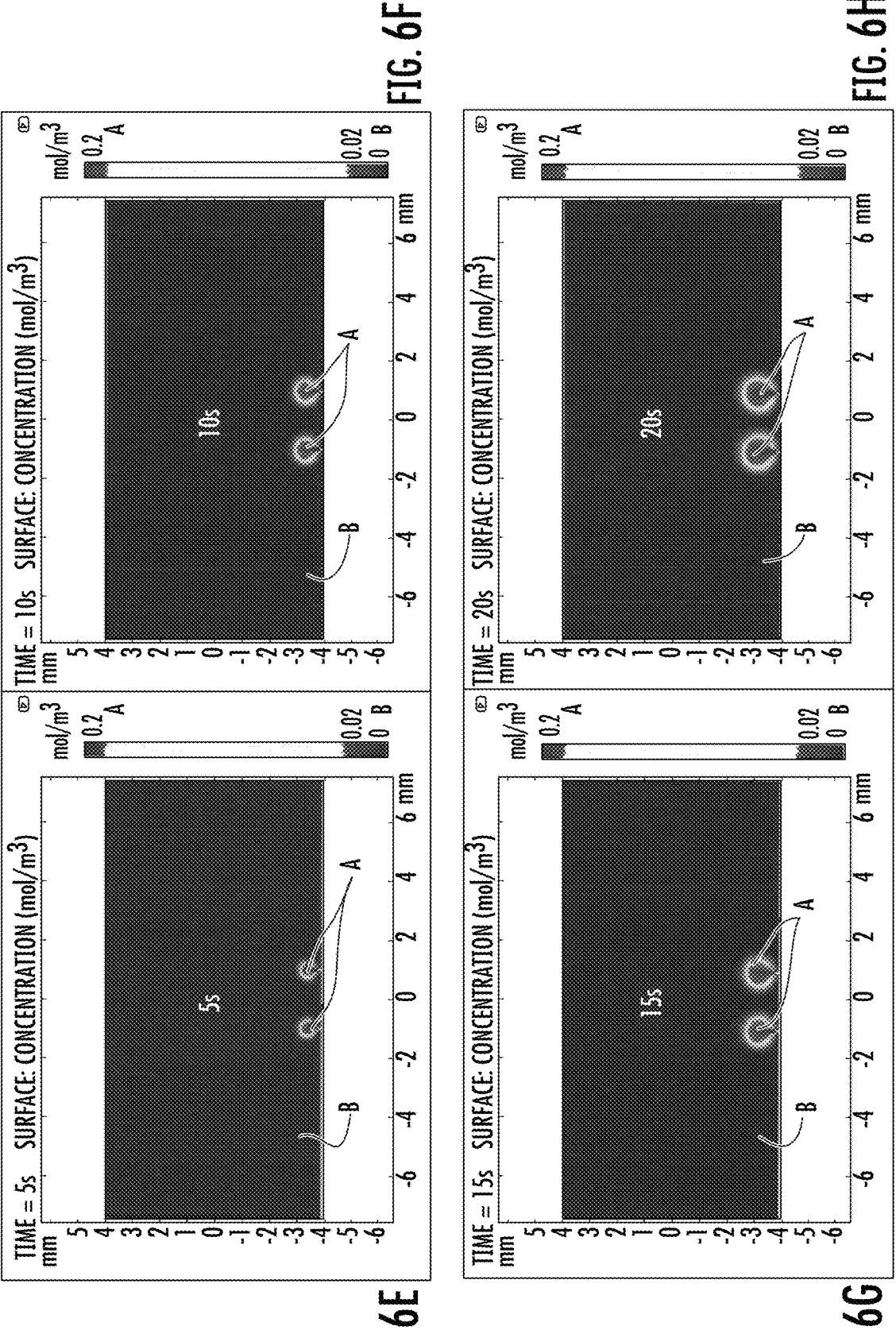
FIGS. 6E-6H are plots showing time points at: 5 s (E), 10 s (F), 15 s (G), and 20 s (H), respectively.

With continued pressures as shown in the images of FIGS. 6E-6H, there was an appreciable increase in diffusing volumes through the port approaching five seconds. From 1020 seconds of continued application of pressure, the solution begins to disperse over a larger area within the culture similar to dosing a culture traditionally with larger pipettes for a more global/mesofluidic chemical stimulation. Continued pressures post five seconds may be found in the images as 10 seconds (FIG. 6F), 15 seconds (FIG. 6G), and 20 seconds (FIG. 6H). These results highlight the necessity for low pressures, lower concentrations, and shorter (ms) chemical stimulations, and demonstrate the ability to locally apply a defined compound, in this instance, L-Glutamine, through simple 2D/3D microfluidic port integration into the 3D MEA device 30.

These results, however, are not indicative of any one solution for the optimal pressure, concentration, rate of flow, or time for using localized microfluidic perfusion, and serve only as an example of one possible combination of the parameters mentioned. Additionally, while the pressures modelled here are within the range for human actuation, syringe pumps would provide a more controlled application of force for millisecond applications times.

Chemical stimulation in a localized setting such as is modelled here, is vital for more advanced microfluidic applications in open cell culture settings, and could be further tuned through optimization studies for the individual uptake and diffusion characteristics of desired compounds.

In vitro organ-on-a-chip models are becoming increasingly necessary for greatly advancing studies of tissue culture models on the benchtop. By combining new sensing/stimulation modalities on the same substrate 30 as a chip, multifarious data sets may be procured, differential measurements may be compared in real-time, and thus, multifarious datasets may be made possible for the same organ-on-a-chip platform. The 3D MEA device 30 was further functionalized with thermal and analyte sensing modalities on an optically transparent substrate 34 with the addition of microfluidics to configure the penta-modal 3D MEA biosensor device 30.

The thermal sensor capability of the 3D MEA device 30 allowed the IDE 52a to sense changes in physiologically-relevant temperatures, ranging from 22° C. to 42° C., produced by an integrated microheater, which may stabilize temperatures of cell cultures outside of the incubation chamber. Through analysis and modelling of the Nyquist plots, the sensor showed an inverse relationship between temperatures and impedances and indicated the region of most interest was between 1 MHz to 4 MHz, where the elements of the equivalent circuit impacted the first Faradaic region. A linear regression of the measured temperature data produced an R-square value of 0.97506, which in combination with the custom fitting analysis, demonstrated the reliability of this temperature sensor configuration.

The analyte sensor as the IDE 52b capability was addressed much in the same way as the temperature sensor capability, and the capabilities of this platform may be tuned to study any relevant compound of interest by swapping out the antibody used. In this study, the purpose was to measure the concentration of L-Glutamine using the changes of impedance. While the circuit was more complex than, the temperature sensing IDE alone as expected, it was found that similar emphasis could be placed on the 1 MHz to 4 MHz region for this application, based on fitting and Nyquist analysis.

Similarly, a linear regression was performed and the resulting R-square value of 0.90517, validated the sensor's performance, based on the high frequency Faradaic reaction region. The trend observed was an increase in impedance concurrent with increased L-Glutamine concentrations and may be distinguishable from temperature readings. While the results demonstrated reliable results, the robust and repeatable binding of the antibody can be further improved by conjugation chemistry, should orientation of the antibody be desired in future research.

The 3D MEA device 30 capabilities were assessed and demonstrated a 1 kHz impedance of 2.76 kΩ, and a phase signature of −55°, along with an RMS noise signature of ~7.8 μV. These factors indicate potential use in electrophysiological stimulation and recording applications. Optically, the transparent polymer as the substrate 34 provided ample basis for Calcein AM/Propidium Iodide staining, without interference, and additionally demonstrated biocompatibility of the 3D MEA device 30.

The microfluidics integration was demonstrated by simple adjustments to the micromilling of the substrate 34 and replacement of the 3D MEA structures with microfluidic ports. Through COMSOL finite element modelling, localized fluid injection was additionally demonstrated, which may be applied to localized chemical stimulation, nutrient delivery, or even organoid fixation in culture.

The multiple sensing capabilities of the 3D MEA device 30 provide a novel and innovative combination for the realization of biosensors, which have the potential to provide real-time, multiplexed information for organ-on-a-chip systems.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

The invention claimed is:

1. A three-dimensional (3D) microelectrode array device for in vitro electrophysiological applications and penta-modal sensing, comprising:

a substrate comprising a transparent polymer having a top face and opposing bottom face;

a culturing area comprising a transparent polymer on the top face of the substrate;

a plurality of micro vias formed within the substrate and extending from the bottom face to the top face within the culturing area;

a microneedle at each micro via in a first subgroup of the micro vias and extending from the bottom face upward beyond the top face and forming a hypodermic microneedle array on the top face within the culturing area;

metallic traces formed on the bottom face and interconnecting the hypodermic microneedles to form the 3D microelectrode array;

a rastered cut-out formed on the bottom face of the substrate and a microheater positioned within the rastered cut-out on the bottom face of the substrate, said rastered cut-out and microheater positioned to supply heat to the culturing area;

a first set of the plurality of microneedles configured as temperature sensing interdigitated electrodes on the top face adjacent the microheater, and comprising a two-finger circle-in-line configuration, each finger comprising a plurality of metallic contacts forming the electrode in the circle-in-line configuration, and a first set of the metallic traces interconnecting the temperature sensing interdigitated electrodes;

a second set of the plurality of microneedles configured as analyte sensing interdigitated electrodes and comprising a two-finger circle-in-line configuration, each finger comprising a plurality of metallic contacts forming the electrode in the circle-in-line configuration, and a second set of metallic traces interconnecting the analyte sensing interdigitated electrodes; and a second subgroup of the micro vias configured as microfluidic ports within the culturing area.

2. The 3D microelectrode array device of claim 1 wherein the transparent substrate comprises at least one polymer selected from the group consisting of: Polycarbonate, Polystyrene, Poly(methyl methacrylate), Cyclic olefin copolymer, Cyclic olefin polymer, Polyethylene terephthalate, Polyethylene terephthalate glycol, and Polysulfone.

3. The 3D microelectrode array device of claim 2 wherein the transparent substrate is about 100 μm to 5.0 mm in thickness.

4. The 3D microelectrode array device of claim 1 wherein a ring of transparent polymer forming the culturing area comprises at least one polymer selected from the group consisting of: Polycarbonate, Polystyrene, Poly(methyl methacrylate), Cyclic olefin copolymer, Cyclic olefin polymer, Polyethylene terephthalate, Polyethylene terephthalate glycol, and Polysulfone.

5. The 3D microelectrode array device of claim 1 wherein the rastered cut-out is about 100 micrometers square up to about 10 millimeters square.

6. A three-dimensional (3D) microelectrode array device for in vitro electrophysiological applications and pentamodal sensing, comprising:

a substrate comprising a transparent polymer having a top face and opposing bottom face;

a culturing area comprising a transparent polymer on the top face of the substrate;

a plurality of micro vias formed within the substrate and extending from the bottom face to the top face within the culturing area;

a microneedle at each micro via in a first subgroup of the micro vias and extending from the bottom face upward beyond the top face and forming a hypodermic microneedle array on the top face within the culturing area;

metallic traces formed on the bottom face and interconnecting the hypodermic microneedles to form the 3D microelectrode array;

a rastered cut-out formed on the bottom face of the substrate and a microheater positioned within the rastered cut-out on the bottom face of the substrate, said rastered cut-out and microheater positioned to supply heat to the culturing area;

a first set of the plurality of microneedles configured as temperature sensing interdigitated electrodes on the top face adjacent the microheater, and comprising a two-finger circle-in-line configuration, each finger comprising a plurality of metallic contacts forming the electrode in the circle-in-line configuration, and a first set of the metallic traces interconnecting the temperature sensing interdigitated electrodes;

a second set of the plurality of microneedles configured as analyte sensing interdigitated electrodes having conjugated antibodies and comprising a two-finger circle-in-line configuration, each finger comprising a plurality of metallic contacts forming the electrode in the circle-in-line configuration, and a second set of metallic traces interconnecting the analyte sensing interdigitated electrodes; and a second subgroup of the micro vias configured as microfluidic ports within the culturing area.

7. The 3D microelectrode array device of claim 6 wherein the analyte sensing interdigitated electrode includes a gold layer interface for adherence of said conjugated antibodies.

8. The 3D microelectrode array device of claim 7 wherein the analyte sensing interdigitated electrode comprises one or more types of attached antibodies.

9. The 3D microelectrode array device of claim 6 wherein the transparent substrate comprises at least one polymer selected from the group consisting of: Polycarbonate, Polystyrene, Poly(methyl methacrylate), Cyclic olefin copolymer, Cyclic olefin polymer, Polyethylene terephthalate, Polyethylene terephthalate glycol, and Polysulfone.

10. The 3D microelectrode array device of claim 6 wherein the transparent substrate is about 100 μm to 5.0 mm in thickness.

11. The 3D microelectrode array device of claim 6 wherein a ring of transparent polymer forming the culturing area comprises at least one polymer selected from the group consisting of: Polycarbonate, Polystyrene, Poly(methyl methacrylate), Cyclic olefin copolymer, penta Cyclic olefin polymer, Polyethylene terephthalate, Polyethylene terephthalate glycol, and Polysulfone.

12. The 3D microelectrode array device of claim 6 wherein the rastered cut-out is about 100 micrometers square up to about 10 millimeters square.

* * * * *